(12) United States Patent
Behnam

(10) Patent No.: US 11,786,484 B2
(45) Date of Patent: Oct. 17, 2023

(54) XANTHOHUMOL SOLUBILIZATE

(71) Applicant: Aquanova AG, Darmstadt (DE)

(72) Inventor: Dariush Behnam, Rossdorf (DE)

(73) Assignee: Aquanova AG, Darmstadt (DE)

( * ) Notice: Subject to any disclaimer, the term of this patent is extended or adjusted under 35 U.S.C. 154(b) by 189 days.

(21) Appl. No.: 17/258,409

(22) PCT Filed: Jan. 10, 2019

(86) PCT No.: PCT/EP2019/050536
§ 371 (c)(1),
(2) Date: Jan. 6, 2021

(87) PCT Pub. No.: WO2020/011402
PCT Pub. Date: Jan. 16, 2020

(65) Prior Publication Data
US 2022/0125740 A1    Apr. 28, 2022

(30) Foreign Application Priority Data

Jul. 11, 2018  (WO) ................. PCT/EP2018/068729
Jul. 11, 2018  (WO) ................. PCT/EP2018/068731
Jul. 11, 2018  (WO) ................. PCT/EP2018/068801

(51) Int. Cl.
| | | |
|---|---|---|
| A61K 31/12 | (2006.01) | |
| A61K 9/107 | (2006.01) | |
| A61K 47/10 | (2017.01) | |
| A61P 19/02 | (2006.01) | |
| A61K 9/48 | (2006.01) | |
| A61P 29/00 | (2006.01) | |
| A61K 47/26 | (2006.01) | |

(52) U.S. Cl.
CPC .............. *A61K 31/12* (2013.01); *A61K 9/107* (2013.01); *A61K 9/4816* (2013.01); *A61K 9/4825* (2013.01); *A61K 47/10* (2013.01); *A61K 47/26* (2013.01); *A61P 19/02* (2018.01); *A61P 29/00* (2018.01)

(58) Field of Classification Search
None
See application file for complete search history.

(56) References Cited

U.S. PATENT DOCUMENTS

| | | | |
|---|---|---|---|
| 5,629,351 | A | 5/1997 | Taneja et al. |
| 5,972,382 | A | 10/1999 | Majeed et al. |
| 2005/0129791 | A1 | 6/2005 | Babish et al. |
| 2007/0104741 | A1 | 5/2007 | Murty et al. |
| 2008/0220102 | A1 | 9/2008 | Behnam |
| 2009/0087419 | A1 | 4/2009 | Sakai et al. |
| 2009/0208472 | A1 | 8/2009 | Sakai et al. |
| 2010/0029757 | A1 | 2/2010 | Hellerbrand |
| 2010/0098676 | A1 | 4/2010 | Gokaraju et al. |
| 2011/0086017 | A1 | 4/2011 | Kravets et al. |
| 2011/0129546 | A1 | 6/2011 | Mill |
| 2011/0207697 | A1* | 8/2011 | Ono ........................ A61P 31/04 |
| | | | 514/685 |
| 2011/0293678 | A1 | 12/2011 | Behnam |
| 2015/0342881 | A1 | 12/2015 | Behnam |
| 2016/0008298 | A1 | 1/2016 | Stevens |
| 2016/0022569 | A1 | 1/2016 | Tonge et al. |
| 2016/0074316 | A1 | 3/2016 | Caetano et al. |
| 2016/0081975 | A1 | 3/2016 | Bromley |
| 2017/0042835 | A1 | 2/2017 | Singh |
| 2019/0314326 | A1 | 10/2019 | Garti et al. |
| 2020/0129452 | A1 | 4/2020 | Behnam |
| 2020/0222346 | A1 | 7/2020 | Behnam |
| 2022/0202713 | A1 | 6/2022 | Behnam |

FOREIGN PATENT DOCUMENTS

| | | |
|---|---|---|
| CN | 104720070 A | 6/2015 |
| CN | 106619588 B | 8/2019 |
| DE | 102006024911 A1 | 11/2007 |
| DE | 102006062264 A1 | 6/2008 |
| DE | 202012012130 U1 | 3/2014 |
| EP | 0755940 A1 | 1/1997 |
| EP | 1431385 A1 | 6/2004 |
| EP | 2018869 A1 | 1/2009 |
| JP | H07165588 A | 6/1995 |
| JP | H11500725 A | 1/1999 |
| JP | 2005179213 A | 7/2005 |
| JP | 2009514890 A | 4/2009 |

(Continued)

OTHER PUBLICATIONS

Rawat, Manju, Shailendra Saraf, and Swarnlata Saraf. "Influence of selected formulation variables on the preparation of enzyme entrapped Eudragit S100 microspheres." AAPS pharmscitech 8 (2007): 289-297.

Alexa Kocher et al., "The oral bioavailability of curcuminoids in healthy humans is markedly enhanced by micellar solubilisation but not further improved by simultaneous ingestion of sesamin, ferulic acid, naringenin and kanthohumol", Journal of Functional Foods, vol. 14, Apr. 1, 2015 (Apr. 1, 2015), p. 183-191.

Benham, Copending U.S. Appl. No. 17/258,363, filed Jan. 6, 2021.

Benham, Copending U.S. Appl. No. 17/258,397, filed Jan. 6, 2021.

Bhagat Shivani, Agarwal Monika, Roy Vandana, "Serratiopeptidase: A systematic review of the existing evidence", International Journal Of Surgery, Feb. 1, 2013, Surgical Associates, London, GB, Source info: vol. 11, Nr: 3, pp. 209-217.

Christina Schiborr, Alexa Kocher, Dariush Behnam, Josef Jandasek, Simone Toelstede, Jan Frank, "The oral bioavailability of curcumin from micronized powder and liquid micelles is significantly increased in healthy humans and differs between sexes", Molecular Nutrition & Food Research ,Mar. 1, 2014, Wiley—VCH Verlag, Weinheim, Germany, vol. 58, Nr: 3, pp. 516-527.

(Continued)

*Primary Examiner* — Robert A Wax
*Assistant Examiner* — Quanglong N Truong
(74) *Attorney, Agent, or Firm* — Smartpat PLC

(57) ABSTRACT

In order to provide a formulation for xanthohumol which has an improved anti-inflammatory effect compared to native xanthohumol, the disclosure provides a solubilizate containing, in particular consisting of xanthohumol with a content of less than or equal to 35 wt. %, preferably less than or equal to 15 wt. %, most preferably 9 wt. % to 12 wt. %, and at least one emulsifier having an HLB value in a range between 13 and 18, in particular polysorbate 80 or polysorbate 20 or a mixture of polysorbate 20 and polysorbate 80.

16 Claims, 15 Drawing Sheets

(56) References Cited

FOREIGN PATENT DOCUMENTS

| JP | 2011524884 A | 9/2011 |
|---|---|---|
| JP | 2016505579 A | 2/2016 |
| JP | 2017178866 | 10/2017 |
| RU | 2530056 C2 | 10/2014 |
| WO | 03092664 A1 | 11/2003 |
| WO | 2005092352 A1 | 10/2005 |
| WO | 2007006497 A2 | 1/2007 |
| WO | 2007058480 A1 | 5/2007 |
| WO | 2008065451 A2 | 6/2008 |
| WO | 2012093524 A1 | 7/2012 |
| WO | 2014094921 A1 | 6/2014 |
| WO | 2015171445 A1 | 11/2015 |
| WO | 2016022936 A1 | 2/2016 |
| WO | 2018061007 A1 | 4/2018 |
| WO | 2019011415 A1 | 1/2019 |

OTHER PUBLICATIONS

Dorn et al., "Increased expression of c-Jun in nonalcoholic fatty liver disease", Lab Invest., (20140000), vol. 94, pp. 394-408.
F. Capasso et. al., "Glycyrrhetinic acid, leucocytes and prostaglandins", J. Pharm. Pharmacol. 1983, 35: 332-335.
Hellebrand et al., "Promoterhypermethylation is causing functional relevant downregulation of methylthioadenosine phosphorylase (MTAP) expression in hepatocellular carcinoma", Carcinogenesis, (20060000), vol. 27, pp. 64-72.
K. Gerbeth et al., "Determination of major boswelic acids in plasma by high-pressure liquid chromatography/mass spektrometry", Journal of Pharmaceutical and Biomedical Analysis, vol. 56, No. 5, pp. 998-1005.
Kerstin Gross-Steinmeyer, Patricia L Stapleton, Julia H Tracy, Theo K Bammler, Stephen C Strom, Donald R Buhler, David L Eaton, "Modulation of Aflatoxin B1-Mediated Genotoxicity in Primary Cultures of Human Hepatocytes by Diindolylmethane, Curcumin, and Xanthohumols", Toxicological Sciences,,Dec. 1, 2009,Academic Press, vol. 112, Nr: 2, pp. 303-310.
Khayyal M T, "Novel formulations of Curcumin, Boswellia and Xanthohumol extracts markedly enhance their individual and combined anti-inflammatory activity", EMBASE01 Sep. 2017 (Sep. 1, 2017), Database accession No. EMB-621379886, Retrieved from the Internet: URL:Elsevier Science Publishers, Amsterdam, NL, XP002783955, 1-20 the whole document & Zeitschrift Fur Phytotherapie Sep. 1, 2017 Hippokrates Verlag GmbH NLD,vol. 38, No. Supplement 1, Sep. 1, 2017 (Sep. 1, 2017).
Lini Alappat, Atif B Awad, "Curcumin and obesity: evidence and mechanisms", Nutrition Reviews,,Dec. 1, 2010, International Life Sciences Institute, vol. 68, Nr: 12, pp. 729-738,.
Liu, Chen et al., "Enhanced skin permeation of glabridin using eutectic mixture-based nanoemulsion", Drug Deliv. Transl. Res., 2017, vol. 7, pp. 325-332.
Manju Rawat Singh, Singh Deependra, Swarnlata Saraf, "Development and in vitro evaluation of polar lipid based liposheres for oral delivery of peptide drugs", International Journal of Drug Delivery,,Jul. 31, 2009, vol. 1, Nr: 1, pp. 15-26.
Manju Rawat, Swarnlata Saraf, "Formulation optimization of double emulsification method for preparation of enzyme-loaded Eudragit S100 microspheres", Journal Of Microencapsulation, Jun. 1, 2009, Taylor And Francis, Basingstoke, GB, vol. 26, Nr. 4, pp. 306-314.
Pearson, "Development of Arthritis, Periarthritis and Periostitis in Rats Given Adjuvants". Proceedings of the Society for Experimental Biology and Medicine, vol. 91 issue: 1, pp. 95-101Issue published: Jan. 1, 1956.
Raju Gautam, Sanjay M Jachak, "Recent developments in anti-inflammatory natural products", Publication data: Medicinal Research Reviews, Sep. 1, 2009, New York, NY, US, Source info: vol. 29, Nr: 5, pp. 767-820.
Reji Kizhakkedath, "Clinical evaluation of a formulation containing Curcuma longa and Boswellia serrata extracts in the management of knee osteoarthritis", Molecular Medicine Reports, vol. 8, No. 5, Nov. 1, 2013 (Nov. 1, 2013), p. 1542-1548.
Tominaga et al.: "Licorice flavonoid oil effects body weight loss by reduction of body fat mass in overweight subjects", Journal of Health Science 52(6), 2006, pp. 672-683.
Tominaga et al.: "Licorice flavonoid oil reduced total body fat and visceral fat in overweight subjects: A randomized, double-blind, placebo-controlled study", Obesity Research & Clinical Practice (3), 2009, pp. 169-178.
J. Siemoneit et al., "Inhibition of microsomal prostaglandin E-synthase-1 as a molecular basis for the antiinflammatory actions of boswellic acids from frankincense", British Journal of Pharmacology, vol. 162, No. 1, pp. 147-162.
Wobser et al., "Lipid accumulation in hepatocytes induces fibrogenic activation of hepatic stellate cells", Cell Res, (20090000), vol. 19, pp. 996-1005.
Zamzow Daniel R et al, "Xanthohumol improved cognitive flexibility in young mice", Behavioural Brain Research, vol. 275, Sep. 1, 2014 (Sep. 1, 2014), p. 1-10.
Zeitschrift Fur Phytotherapie Sep. 1, 2017 Hippokrates Verlag Gmbh NLD, Sep. 1, 2017, vol. 38, Supplement 1, ISSN 1438-9584, Abstract.

* cited by examiner

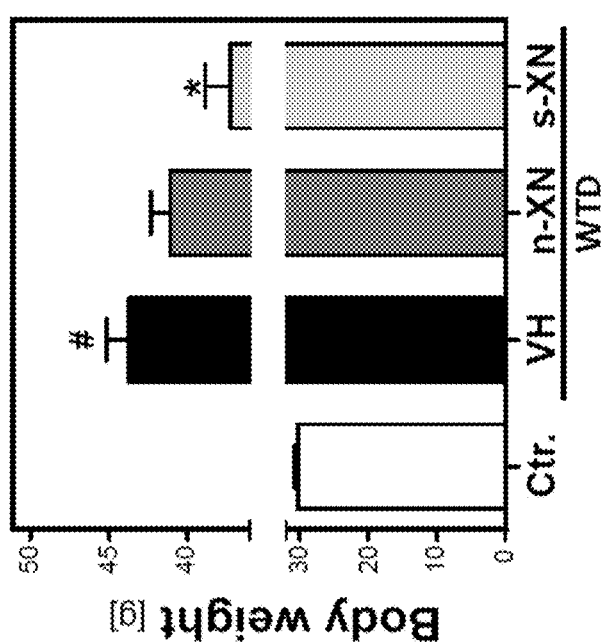
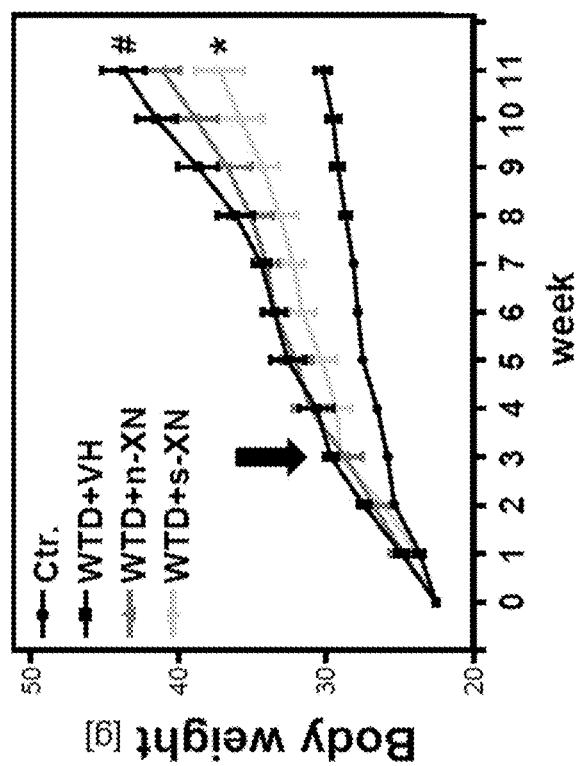
Fig. 1B
Fig. 1A

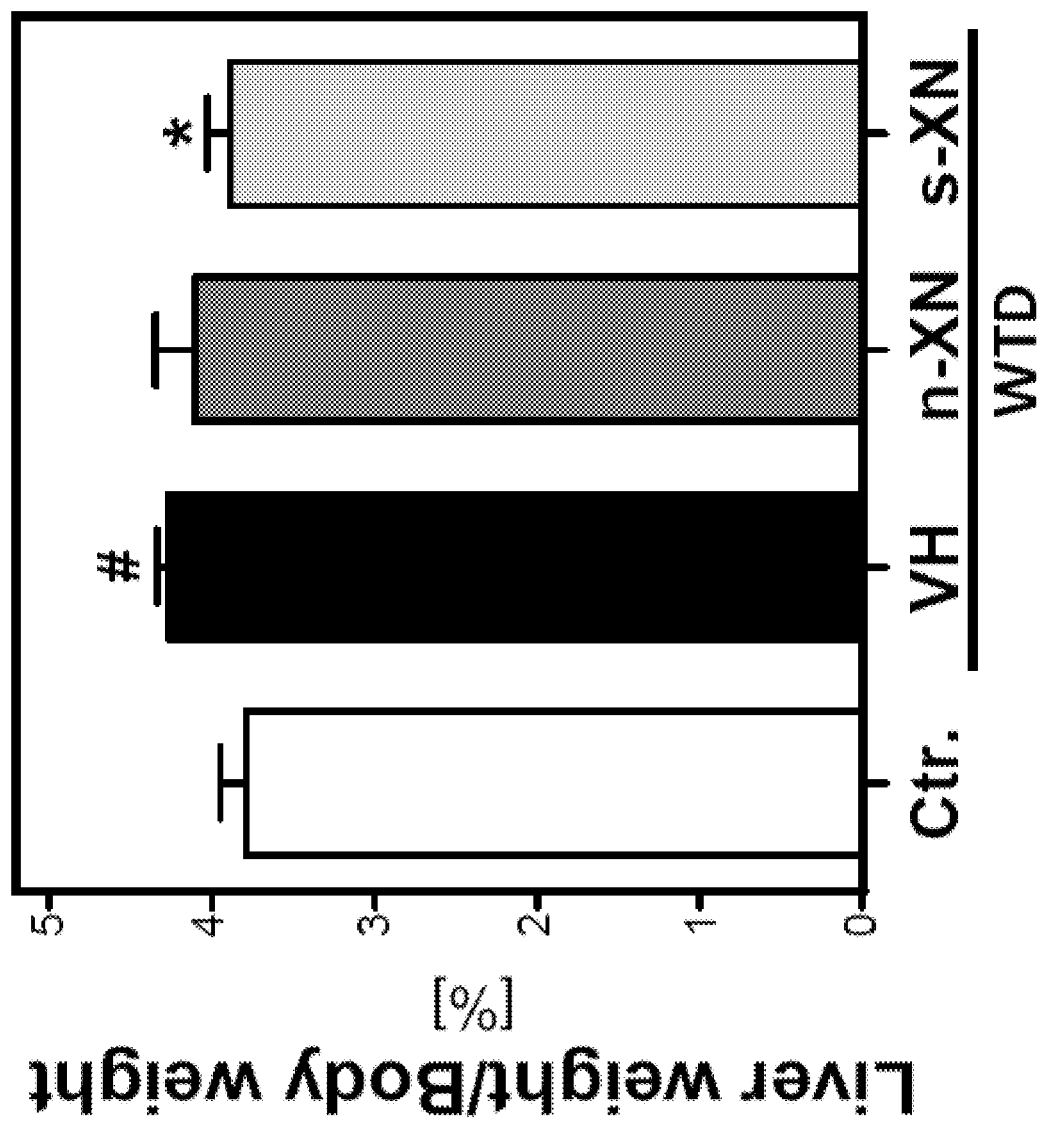

XANTHOHUMOL SOLUBILIZATE

TECHNICAL FIELD

The disclosure relates to an anhydrous solubilizate comprising xanthohumol. Furthermore, the disclosure relates to a fluid containing such a solubilizate, to a capsule filled with such a solubilizate or fluid, and to a pharmaceutical drug or dietary supplement containing such a solubilizate.

BACKGROUND

Xanthohumol is a flavonoid naturally occurring in hops. It is a prenylated plant polyphenol which is classified into the chalcones and has only been identified in hops so far. The bitter hop varieties have a significantly higher content of xanthohumol than aroma varieties. In tests, xanthohumol was found to be effective against the emergence and development of cancer cells. In laboratory experiments, it was moreover found that xanthohumol is capable of protecting the nerve cells of the brain and thus could possibly help to slow down the course of diseases like Alzheimer's or Parkinson's.

For example, http://www.besserlaengerleben.at/gesund-und-fit/hopfen-hilft-gegen-cholesterin-und-blutzucker.html reports about studies according to which xanthohumol seems to lower plasma levels of PCSK9, a protein that plays an important role in cholesterol levels. A reduction in PCSK9 levels could improve the decomposition of LDL cholesterol from the blood. Scientists at Oregon State University have shown in laboratory animals that the intake of large amounts of xanthohumol can lead to improvements in metabolic syndrome and reduced weight gain. These research results could lead to new approaches in treating obesity, high cholesterol and high blood sugar. The combination of these health problems, known as the metabolic syndrome, is nowadays one of the leading causes of death in industrialized countries, besides cardiovascular diseases and type 2 diabetes.

Xanthohumol occurs naturally in hops and therefore in beer. The highest levels used in the study would be equivalent to a human dose of 350 milligrams per day for one person. However, this value clearly exceeds what can be achieved by normal intake of food. However, intake through a dietary supplement would theoretically be possible without problems.

Hop extracts are currently commercially available as dietary supplements. However, it has been found that the bioavailability of xanthohumol is quite low when the hops extracts are taken orally.

SUMMARY

It is therefore an object of the invention to provide a formulation for xanthohumol which exhibits improved bioavailability compared to native xanthohumol from hop extracts.

A further object of the invention is to provide a formulation for xanthohumol which brings about an improved anti-inflammatory effect compared to native xanthohumol without chemically altering the active substance xanthohumol.

These objects are achieved by the invention in a surprisingly simple way with a solubilizate according to claim 1.

The invention provides a solubilizate containing, in particular consisting of xanthohumol with a content of less than or equal to 75 wt. %, preferably less than or equal to 70 wt. %, more preferably less than or equal to 35 wt. %, yet more preferably less than or equal to 15 wt. %, most preferably 2 wt. % to 12 wt. %, and at least one emulsifier having an HLB value in the range between 13 and 18, in particular selected from the group consisting of polysorbate 80 and polysorbate 20, sucrose ester of edible fatty acids (E 473), and phospholipids, especially lecithin, and mixtures of at least two of the emulsifiers mentioned. As will be discussed in more detail further below, the solubilizate of the invention exhibits improved bioavailability compared to native xanthohumol from hop extracts and an improved anti-inflammatory effect compared to native xanthohumol.

The solubilizate according to the invention is a mixture of colloidal formulation in the form of a capsule filling which contains xanthohumol as a bioactive substance. The invention allows to prepare a solubilizate with micelles that are stable even under physiological conditions already from emulsifier and xanthohumol alone. However, the solubilizate may also be a mixture which, in addition to xanthohumol, mainly consists of technical additives, carriers, fillers, and stabilizers. The solubilizate of the invention is in particular anhydrous, or non-aqueous. It is designed to be used as a capsule filling. It is in particular liquid, but is not a beverage.

A prerequisite for the absorption of fat-soluble micronutrients by the human or animal body is the formation of what is known as "physiological mixed micelles" with the help of bile acids, bile salts, and enzymes from the digestive tract. The solubilizate according to the invention therefore has a stable micellar structure similar to this natural principle and with the background intension of optimizing the bioavailability of xanthohumol. Enhancement in bioavailability can be achieved in this way if the micelle proves to be stable under physiological conditions, i.e. at a temperature of 37° C. and at pH 1.1, so as to reach the small intestine unimpaired.

In an advantageous embodiment of the invention it is contemplated that the solubilizate contains an ethanolic extract of the hard resins from hops as a source of xanthohumol, due to the high content of xanthohumol, with a xanthohumol concentration in this extract in a range between 60 wt. % and 95 wt. %, preferably in a concentration in a range from 65 wt. % to 85 wt. %. In particular the products "Xantho-Flav Pur" or "Xantho-Flav" can be used as a xanthohumol source in the context of the invention and will be discussed in more detail further below.

In a preferred embodiment, the solubilizate according to the invention contains polysorbate 80 or polysorbate 20 or a mixture of polysorbate 20 and polysorbate 80 as an emulsifier. The invention advantageously provides the possibility of allowing to choose the emulsifier or emulsifier composition for producing micelles of xanthohumol that are stable even under physiological conditions (pH 1.1 and 37° C.). For example, it is also possible to use at least one sucrose ester of an edible fatty acid or a mixture of multiple sucrose esters of edible fatty acids as the emulsifier. The inventor has moreover found that a mixture of polysorbate 80 or of polysorbate 20 or of a mixture of polysorbate 80 and polysorbate 20 with at least one sucrose ester of an edible fatty acid can also be used as an emulsifier within the scope of the invention. Furthermore, a mixture of at least one phospholipid, for example lecithin, with at least one sucrose ester of an edible fatty acid can be used as an emulsifier in the context of the invention.

Thus, the invention offers the advantage of allowing to adapt the composition depending on which other components are to be contained in the solubilizate and in which amounts, its properties in terms of bioavailability, storage stability, and interactions with the material of the capsules in which the solubilizate is intended to be provided for oral use.

It has been found that, depending on how much xanthohumol is to be solubilized, and in particular also depending on the question of whether further active substances are intended to be micellized in addition to xanthohumol, the mass ratio of emulsifier, in particular of polysorbate 80, to xanthohumol can be adjusted in a range between 30:1 and 3:1, preferably in the range between 25:1 and 5:1, more preferably in the range between 9.8:1 to 6.6:1.

For this purpose, the emulsifier content, in particular the polysorbate content according to the invention is at least 45 wt. %, preferably in a range between 60 wt. % and 95 wt. %, most preferably in the range between 73 wt. % and 90 wt. %. Depending on how much emulsifier can be used for a specific application case of the solubilizate, the invention offers the possibility for the solubilizate to contain ethanol in an amount of up to 35 wt. %, preferably up to 20 wt. %, most preferably up to 15 wt. %. The content of polysorbate can be reduced by adding ethanol, which is an advantage with regard to the ADI value for polysorbate.

According to an advantageous embodiment of the invention it is contemplated that the solubilizate contains up to 8 wt. %, preferably up to 5 wt. % of curcumin. According to the inventor's findings, curcumin has the potential as a synergist for the anti-inflammatory effect of xanthohumol.

Furthermore, the invention provides the possibility for the solubilizate to contain up to 7 wt. %, preferably up to 5 wt. % of glavonoid. Glavonoid is the trade name of an oil containing licorice flavonoid (Licorice Flavonoid Oil, LFO) consisting of hydrophobic polyphenols from licorice in medium-chain triglycerides. It is thought to have a weight-reducing effect, which is associated with reduced body fat. It should also be noted that ethanolic extracts of liquorice are ascribed antioxidant properties. For the formation of stable micelles it can be helpful if the solubilizate contains up to 25 wt. %, preferably up to 10 wt. % of glycerol, depending on which active substances are to be solubilized and in which amount. Also, the amount of polysorbate can be reduced by adding glycerol.

The solubilizates of the invention exhibit a narrow particle size distribution with a small mean particle size, even under the physiological conditions of a gastric passage; the distribution of the diameter of the micelles in a dilution of the solubilizate with distilled water in a ratio of 1:500 at pH 1.1 and 37° C. ranges from about d10=70 nm to about d90=160 nm. These values were determined based on an intensity distribution. Details regarding the particle size analysis of the micelles of the solubilizates will be discussed further below.

The invention advantageously provides solubilizates with very good anti-inflammatory properties. The anti-inflammatory activity of the xanthohumol solubilizate measured as the concentration of C-reactive protein (CRP) in the blood serum of arthritic rats after a single administration of the solubilizate in a dose of 5 mg/kg body weight is in the range from about 2500 pg/ml to about 2700 pg/ml and, thus, is significantly lower than the concentration of C-reactive protein (CRP) in the blood serum of arthritic rats after a single administration of native xanthohumol in a dose of 5 mg/kg body weight, which is in the range from about 3300 pg/ml to about 3700 pg/ml. For this, see the attached FIG. 1c and the description thereof further below.

The anti-inflammatory activity of a solubilizate according to the invention comprising xanthohumol and curcumin, measured as the concentration of C-reactive protein (CRP) in the blood serum of arthritic rats after a single administration of the solubilizate in a dose of 5 mg/kg body weight of each of xanthohumol and curcumin is in the range from about 2000 pg/ml to about 2400 pg/ml and, thus, is significantly lower than the concentration of C-reactive protein (CRP) in the blood serum of arthritic rats after a single administration of native xanthohumol and native curcumin in a dose of 5 mg/kg body weight each, which is in the range from about 3200 pg/ml to about 3600 pg/ml. For this, see the attached FIG. 1b and the associated description thereof further below.

The anti-inflammatory activity of a xanthohumol solubilizate according to the invention, measured as the concentration of myeloperoxidase (MPO) in the blood serum of arthritic rats after a single administration of the solubilizate in a dose of 5 mg/kg body weight is in a range from about 800 mU/ml to about 900 mU/ml and, thus, is significantly lower than the concentration of myeloperoxidase (MPO) in the blood serum of arthritic rats after a single administration of native xanthohumol in a dose of 5 mg/kg body weight, which is in the range from about 1100 mU/ml to about 1200 mU/ml. For this, see the attached FIG. 4 and the associated description thereof further below.

The enzyme unit (U) is a unit which has since been replaced by the katal (kat) to indicate enzymatic activity. Since the numerical values change when katal is used, the enzyme unit (U) continues to be used in medicine and clinical chemistry. One enzyme unit U corresponds to one micro-mole of substrate conversion per minute.

The anti-inflammatory effect of a solubilizate according to the invention comprising xanthohumol and curcumin, measured as the concentration of myeloperoxidase (MPO) in the blood serum of arthritic rats after a single administration of the solubilizate in a dose of 5 mg/kg body weight of xanthohumol and curcumin each is in a range from about 550 mU/ml to about 600 mU/ml and, thus, is significantly lower than the concentration of myeloperoxidase (MPO) in the blood serum of arthritic rats after a single administration of native xanthohumol and native curcumin in a dose of 5 mg/kg body weight each, which is in the range from about 1100 mU/ml to about 1300 mU/ml. For this, see the attached FIG. 3 and the associated description thereof further below.

An indication of the improved bioavailability compared to native xanthohumol or to compositions of xanthohumol with curcumin and/or glavonoid that are not micellized according to the invention is obtained by determining the turbidity of the solubilizate, which is clearly more easily accessible in terms of measurement technology. As a result of the inventive formulation, the solubilizate preferably exhibits a turbidity of less than 100 FNU, more preferably less than 50 FNU, measured by scattered light measurement using infrared light according to the specifications of the ISO 7027 standard at a dilution of the solubilizate in a ratio of 1:50 in water at pH 1.1 and 37° C.

The correlation between the load of a micelle with xanthohumol and its stability is inversely proportional. Accordingly, an increase in load leads to greater instability of the micelle. Only the intact micelles cause an increase in bioavailability. As becomes evident from the narrow particle size distributions and also the extremely low turbidity of the solubilizates according to the invention, the invention offers the great advantage of providing highly loaded stable micelles which are also stable under physiological conditions and therefore achieve high bioavailability of xanthohumol.

In order to facilitate oral application of the solubilizate of the invention in a more simple and convenient way for the consumer or patient, the invention furthermore provides a capsule filled with an anhydrous solubilizate as described above, which capsule is in the form of a soft gelatin capsule or a hard gelatin capsule or a soft gelatin-free capsule or a hard gelatin-free capsule, in particular a cellulose capsule.

Within the context of the invention, the solubilizate according to the invention may furthermore be incorporated into other fluids, in particular liquids, and the small micelles filled with active substance will be preserved when doing so. Thus, the invention also provides a fluid containing the solubilizate as described above, wherein the fluid is selected from the group consisting of foods, beverages, cosmetics, and pharmaceutical products. The fluid may in particular comprise an aqueous dilution of the solubilizate.

Thus, the invention also provides for the use of a solubilizate or of a fluid as described above as a dietary supplement and/or as a pharmaceutical drug for the treatment of diseases involving inflammation, cancer, Alzheimer's, Parkinson's, obesity, high cholesterol levels, elevated blood sugar, diabetes, metabolic syndrome, and/or autoimmune diseases, multiple sclerosis (MS), for reducing visceral fat, for thermogenesis, as a cholesterol-lowering dietary supplement and/or pharmaceutical drug, in particular with regard to LDL cholesterol, and/or as a dietary supplement and/or pharmaceutical drug with an effect for lowering glucose in the blood and/or triglycerides in the blood, for improving macular pigment density, for reducing oxidative stress and/or for reducing the accumulation of fat in the hepatocytes, in particular as a dietary supplement and/or pharmaceutical drug with an effect against fatty liver, Friedreich's ataxia, lysosomal diseases, in particular Tay-Sachs disease, arteriosclerosis, heart diseases, arthritis.

The invention furthermore provides a method for treating diseases involving inflammation, cancer, Alzheimer's, Parkinson's, obesity, high cholesterol levels, elevated blood sugar, diabetes, metabolic syndrome, and/or autoimmune diseases, multiple sclerosis (MS), for reducing visceral fat, for thermogenesis, for lowering cholesterol, in particular LDL cholesterol, and/or for lowering glucose in the blood and/or triglycerides in the blood, for improving macular pigment density, for reducing oxidative stress and/or for reducing the accumulation of fat in the hepatocytes, for treating Friedreich's ataxia, lysosomal diseases, in particular Tay-Sachs disease, arteriosclerosis, heart diseases, arthritis; which method comprises administering to the patient a solubilizate as described above, in particular in a capsule or as a fluid, in particular orally. In a preferred embodiment of the method according to the invention, the solubilizate is administered to the patient in a dose of xanthohumol ranging from 0.5 mg/kg body weight to 1 mg/kg body weight, preferably in a dose of 0.81 mg/kg body weight, in particular once daily.

In a further preferred embodiment of the method according to the invention, the solubilizate is administered to the patient in a dose of xanthohumol ranging from 0.5 mg/kg body weight to 1 mg/kg body weight, preferably in a dose of 0.81 mg/kg body weight of xanthohumol, and at the same time in a dose of curcumin ranging from 0.5 mg/kg body weight to 1 mg/kg body weight, preferably in a dose of 0.81 mg/kg body weight, in particular once daily.

The invention furthermore provides a method for producing a solubilizate with xanthohumol as described above, the method comprising the steps of:
(a) providing an ethanolic extract of the hard resins from hops, in particular Xantho-Flay Pure powder;
(b) adding polysorbate 80 and/or polysorbate 20 and/or a mixture of polysorbate 20 and polysorbate 80;

wherein step (b) comprises heating to a temperature in a range from 80° C. to 95° C., preferably to a temperature in a range from 81° C. to 90° C., most preferably to a temperature in a range from 83° C. to 87° C. This allows to bring about stable micellization of the xanthohumol in a simple and reliable way.

In an alternative embodiment, the method according to the invention can be performed with the following steps:
(a) providing at least one emulsifier with an HLB value in a range between 13 and 18, in particular selected from the group consisting of polysorbate 80, polysorbate 20, sucrose esters of edible fatty acids (E 473), and phospholipids, in particular lecithin, and mixtures of at least two of the emulsifiers mentioned;
(b) adding ethanol;
(c) heating to a temperature of up to 85° C., preferably up to 80° C., while mixing, for example by stirring;
(d) adding an ethanolic extract of the hard resins from hops, in particular Xantho-Flav Pure powder and/or Xantho-Flav powder while mixing, for example by stirring;

wherein step (d) comprises heating to a temperature in a range from 80° C. to 95° C., preferably to a temperature in a range from 81° C. to 90° C., most preferably to a temperature in a range from 83° C. to 87° C.

If the solubilizate according to the first variant of the method is desired to furthermore contain ethanol, the invention contemplates that step (b) is preceded by a step
(b1) of dissolving in ethanol the ethanolic extract of the hard resins from hops, in particular Xantho-Flav Pure powder, while heating to a temperature in a range from 40° C. to 62° C., preferably to a temperature in a range from 45° C. to 57° C., most preferably to a temperature in a range from 48° C. to 52° C.

In any case, if necessary, step (c) may comprise heating to a lower temperature in a range from 40° C. to 62° C., preferably to a temperature in a range from 45° C. to 57° C., most preferably to a temperature in a range from 48° C. to 52° C.

Furthermore within the context of the invention, depending on which emulsifier composition was selected for the respective application case, step (b) may comprise adding a phospholipid, in particular adding lecithin, together with ethanol. It is also possible in step (b) to add glycerol and/or water together with ethanol.

If co-micellization of xanthohumol with curcumin and/or with glavonoid is intended, the invention provides the following variant of a preparation method comprising the steps of
(a) providing polysorbate 80 and/or polysorbate 20 and/or a mixture of polysorbate 20 and polysorbate 80;
(b) adding an ethanolic extract of the hard resins from hops, in particular Xantho-Flav Pure powder;
wherein
curcumin powder is added prior to step (b) or after step (b); and
step (a) comprises heating to a temperature in a range from 40° C. to 62° C., preferably to a temperature in a range from 45° C. to 57° C., most preferably to a temperature in a range from 48° C. to 52° C.; and
wherein
step (b) comprises heating to a temperature in a range from 60° C. to 75° C., preferably to a temperature in a range from 61° C. to 70° C., most preferably to a temperature in a range from 63° C. to 67° C.

In a refinement of this method, step (b) can be preceded by a step (b1) of adding ethanol at a temperature in a range from 40° C. to 62° C., preferably at a temperature in a range from 45° C. to 57° C., most preferably at a temperature in a range from 48° C. to 52° C.

Furthermore, step (b1) can be preceded by a step (b11) of adding glycerol at a temperature in a range from 40° C. to 62° C., preferably at a temperature in a range from 45° C. to 57° C., most preferably at a temperature in a range from 48° C. to 52° C.

In a refinement of these variants for the preparation of solubilizates according to the invention, it is contemplated that curcumin powder is added prior to step (b1) at a temperature in a range from 50° C. to 72° C., preferably at a temperature in a range from 55° C. to 67° C., most preferably at a temperature in a range from 58° C. to 62° C.; or after step (b) at a temperature in a range from 70° C. to 92° C., preferably at a temperature in a range from 75° C. to 87° C., most preferably at a temperature in a range from 78° C. to 82° C.

Optionally, for this purpose, step (b) can be followed by a further step (c) of adding glavonoid while heating to a temperature in a range from 80° C. to 97° C., preferably to a temperature in a range from 83° C. to 92° C., most preferably to a temperature in a range from 85° C. to 89° C.

BRIEF DESCRIPTION OF THE DRAWINGS

FIG. 1A is a graph showing weight gain and (visceral) fat accumulation.

FIG. 1B is a graph showing weight gain and (visceral) fat accumulation.

FIG. 2B is a graph showing liver weights.

DETAILED DESCRIPTION

Figure 1C:
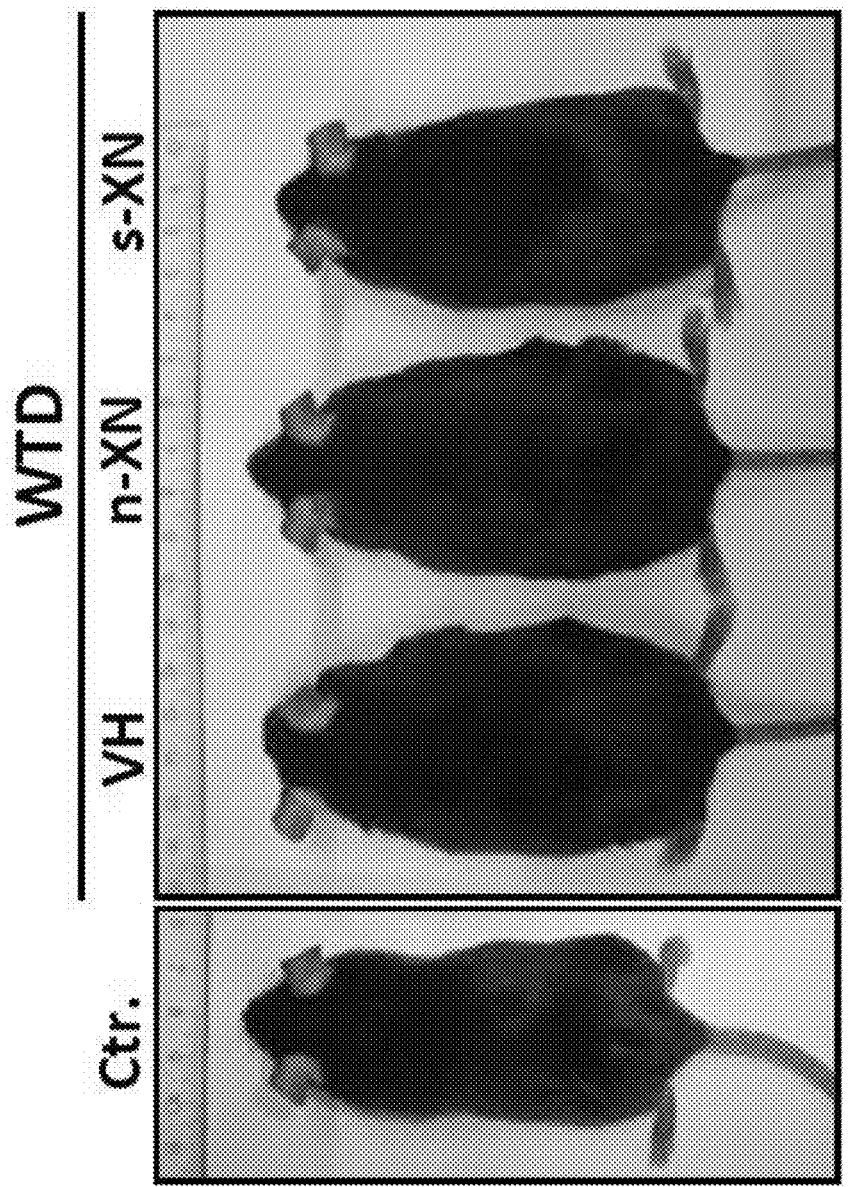
FIG. 1C is a photograph of test animals.

The invention will now be explained in more detail by way of exemplary embodiments. The following components were used:

Xanthohumol

The products "Xantho-Flav Pure" or "Xantho-Flav 75% (65-85%)" of the brand "Hopsteiner" by Simon H. Steiner, Hopfen, GmbH, Mainburg, Germany were used as the xanthohumol source. Both are natural products produced from hops. The active substance is the hop polyphenol xanthohumol. This is a yellow colored powder with a xanthohumol content of at least 85% in the case of "Xantho-Flav Pure" according to manufacturer's specifications. The xanthohumol content of "Xantho-Flav 75% (65-85%)" was at least 70% in the exemplary embodiments presented below. The concentrations of xanthohumol and isoxanthohumol in "Xantho-Flav Pure" are quantified by the manufacturer according to UV spectrophotometric analysis or HPLC EBC 7.8 using external calibration standard pure XN (370 nm) or IX (290 nm). "Xantho-Flav Pure" contains the prenylated flavonoid xanthohumol in a very high concentration. "Xantho-Flav Pure" of batch number 9432 was used for the exemplary embodiments in the context of the present application.

Polysorbate 80

The source of polysorbate 80 was the material "TEGO SMO 80 V FOOD" with the specification code "K04 EU-FOOD" from Evonik Nutrition & Care GmbH, Essen, Germany. The product complies with the EU requirements for food additive E 433. As an alternative to the TEGO SMO 80 V from Evonik mentioned above, it is also possible to use TEGO SMO 80 V from InCoPA Gmbh, Illertissen, Germany, or Crillet 4/Tween 80-LQ-(SG) from CRODA GmbH, Nettetal, Germany, or Lamesorb SMO 20 and Kotilen-O/1 VL from Univar or from Kolb Distributions AG, Hedingen, Switzerland, as the polysorbate 80 in the exemplary embodiments described below.

Sucrose Esters of Edible Fatty Acids (E473)

Sucrose esters of edible fatty acids (E 473) that can be used include individual sucrose esters of edible fatty acids (E 473) or mixtures of at least two sucrose esters of edible fatty acids. More particularly, suitable sucrose esters of edible fatty acids include sucrose monolaurate, sucrose dilaurate, sucrose monopalmitate, sucrose dipalmitate, sucrose monostearate, and sucrose distearate. The products "Ryoto L-1695", "Ryoto P-1670", and "Ryoto M-1695" from manufacturer Mitsubishi-Kagaku Foods Corporation were used for the exemplary embodiments described below. Furthermore, the product "DUB SE 16 P" from manufacturer Stéarinerie Dubois was used as a sucrose esters of edible fatty acids (sucrose ester E 473). The product "DUB SE 16 S" may likewise be used to produce xanthohumol solubilizates according to the invention.

The phospholipid used was lecithin in the form of the product "Epikuron® 135 F" or "Epikuron® 135 F IP (GMO-free) (35% or 32% of phosphatidylcholine in soybean oil)" from Cargill Inc.

Glycerol

The product used as the glycerol in the context of the present application was "Glycamed 99.7%" from Glaconchemie GmbH, Merseburg, Germany. The glycerol content of this product is at least 99.5% according to manufacturer's specifications.

Ethanol

In the context of the present application, ethanol was purchased from Berkel Pfalzische Spritfabrik GmbH & Co. KG. According to the specification for "undenatured neutral alcohol 1411U taxed", the content of ethanol of this product is about 94±1%.

Curcumin

The product named "Turmeric Oleoresin Curcumin Powder 95%" with product code EP-5001 from Green Leaf Extraction Pvt Ltd., Kerala, India, was used as the curcumin. The curcumin powder has CAS Number 458-37-7. It is a natural product obtained by solvent extraction of the rhizomes of Curcuma Longa. The curcumin content of the powder is at least 95%, according to manufacturer's specifications. This curcumin content is determined by ASTA method 18.0.

As an alternative to the "oleoresin turmeric 95%" curcumin powder from Green Leaf mentioned above, it is also possible for the exemplary embodiments described below to use, as the curcumin, 95% curcumin extract from Neelam Phyto-Extracts, Mumbai, India, or curcumin BCM-95-SG or curcumin BCM-95-CG from eurochem GmbH, Grobenzell, Germany, or Curcuma Oleoresin 95% from Henry Lamotte OILS GmbH, Bremen, Germany, for example.

Glavonoid

"Glavonoid" is the product name for a composition of Kaneka Corporation, Osaka, Japan, which contains glabridin as an active substance. Glabridin is a flavonoid of the licorice plant (Glycyrrhiza glabra). The product "Kaneka Glavonoid" contains 30% of licorice extract and 70% of edible oil, according to the manufacturer. "Kaneka Glavonoid" is standardized to 3% glabridin, according to the manufacturer, which is the main component of the polyphenols of the licorice plant. The CAS number of glabridin is 59870-68-7.

Water was used in the form of distilled water.

The particle size analyzes of the micelles in aqueous dilutions of solubilizates according to the invention were measured according to the principle of dynamic light scattering using laser light of 780 nm wavelength. The particle size measurements were performed using the ParticleMetrix NANOFLEX backscatter particle analyzer. The measuring principle is based on dynamic light scattering (DLS) in a 180° heterodyne backscattering setup. With this geometry, part of the laser beam is mixed into the scattered light (heterodyne technique). Because of the short light path of 200 micrometers to 300 micrometers within the sample, backscattering is an advantage for absorbent and highly concentrated samples. The heterodyne technique has an enhancing effect on the signal-to-noise ratio and on the sensitivity of the sub-100 nm range.

The laser light is injected into the Y-fork of an optical fiber. What returns in the same fiber is the laser light partially reflected at the sapphire window of the sample chamber and the light backscattered from the sample. The detector in the second leg of the Y fork captures the interfering signals. Fast Fourier transform evaluation analyses the fluctuating stray light components to give a frequency-dependent power spectrum. Each frequency component represents a Brownian diffusion constant and can therefore be assigned to a particle size. Stokes-Einstein relation is used for conversion into a particle size distribution:

$$D = k \frac{T}{3\pi \eta d_P}$$

This equation includes the diffusion constant D, Boltzmann's constant k, temperature T, dynamic viscosity $\eta$ of the medium, and the diameter $d_p$ of the particles. A temperature sensor is arranged near the sapphire window close to the sample in the measurement device.

For the experimental determination of turbidity of the solubilizates according to the invention, the turbidity meters are calibrated with a standard suspension. Thus, instead of measured light intensity, the concentration of the calibration suspension is indicated. So, when any arbitrary suspension is measured, the indication means that the respective liquid causes the same light scattering as the standard suspension at the indicated concentration. The internationally defined turbidity standard is formazin. One of the most common units is the indication in FNU, i.e. Formazin Nephelometric Units. This is the unit used in water treatment, for example, for measuring at 90° in compliance with the requirements of the ISO 7072 standard.

Exemplary Embodiment 1

10% Xantho Flay Pur-Solubilizate

The following is used:

| 100 g | Xantho-Flav Pur, and |
|---|---|
| 900 g | polysorbate 80. |

For this purpose, the Xantho-Flav Pure powder is incorporated into Polysorbate 80 by stirring. The powder is added at an appropriate rate so as to be evenly drawn into the emulsifier. Homogenization is continued while heating to 83 to 87° C. Once a homogeneous solubilizate has been obtained, the latter is cooled to a temperature below 60° C. The Xantho-Flav solubilizate is then bottled and stored in the dark and cool, i.e. below 25° C.

Exemplary Embodiment 2

10% Xantho Flay Pur-Solubilizate with Ethanol

For this variant of a xanthohumol solubilizate according to the invention, the following is used:

| | |
|---|---|
| 100 g | Xantho-Flav Pur, |
| 150 g | ethanol (96%) of neutral alcohol type 1411U, and |
| 750 g | polysorbate 80. |

First, the Xantho-Flav Pure powder is dissolved in ethanol while being heated to a temperature in the range between 48 and 52° C. A homogeneous solution is created. Polysorbate 80 is then added into the solution of Xantho-Flav Pure in ethanol while heating to between 83 and 87° C. The adding is done at a rate such that the two fluids homogenize well under stirring. The resulting solubilizate is cooled to below 60° C. and is bottled and stored in the dark and cool, i.e. at temperatures below 25° C.

Exemplary Embodiment 2A

A 10% Xantho Flay Pur-solubilizate with ethanol may also be produced with less ethanol and more polysorbate 80.

For this variant of a xanthohumol solubilizate according to the invention, the following is used:

| | |
|---|---|
| 100 g | Xantho-Flav Pur, |
| 100 g | ethanol (96%) of neutral alcohol type 1411U, and |
| 800 g | polysorbate 80. |

First, the Xantho Flay Pure powder is dissolved in ethanol while being heated to a temperature in the range between 56 and 60° C. A homogeneous solution is created. The further preparation is as in exemplary embodiment 2.

Exemplary Embodiment 3

12% Xantho Flay Pur-Solubilizate with Ethanol

The following is used for its preparation:

| | |
|---|---|
| 120 g | Xantho Flay Pur, |
| 150 g | ethanol (96%) neutral alcohol type 1411U, and |
| 730 g | polysorbate 80. |

The 12% Xantho-Flav Pure solubilizate is prepared in the same way as in exemplary embodiment 2.

The produced solubilizates are dark brown and flow well, despite being slightly viscous. Dissolved in water with a ratio of 1:50 at about 40 to 50° C., a dark yellow to ocher-colored, slightly hazy solution is produced. In the case of 10% Xantho Flay solubilizate with ethanol, HPLC measurements confirmed the content of 10% of Xantho Flay included in the micelles. The density of this solubilizate was determined by hydrometer measurement at 20° C. to be 1 to 1.1 g/cm$^3$. The pH of the solubilizate was between 5 and 7 for the solution prepared with water with a ratio of 1:50. The total number of germs was less than or at most equal to 1,000/g. Yeasts and molds were at 100/g maximum, and no E. coli or coliform bacteria were detected in 1 g of solubilizate according to the Ph. Eur. method of the version valid in October 2014.

For the xanthohumol solubilizate with ethanol according to exemplary embodiment 2, turbidity measurements were made for a dilution in water with a ratio of 1:50 at a pH of 1.1 and a temperature of 37° C., i.e. under physiological conditions. The value averaged over three samples is 40.9 FNU, calculated from individual values of 26.0 FNU, 6.4 FNU, and 90.2 FNU.

For the particle size measurement of the xanthohumol solubilizate with ethanol according to exemplary embodiment 2, the solubilizate was first diluted with distilled water in a ratio of 1:500 and brought to 37° C. under continuous stirring using a magnetic stirrer and a hot plate. The pH was then adjusted to 1.1 using 32% hydrochloric acid. The samples were then immediately measured. The results of the intensity distribution are compiled in the table below.

| $d_{10}$ (nm) | $d_{50}$ (nm) | $d_{90}$ (nm) | $d_{99}$ (nm) |
|---|---|---|---|
| 76.90 | 107.0 | 155.3 | 212.9 |

Exemplary Embodiment 4

A xanthohumol solubilizate according to the invention may also be produced with the addition of glycerol. In particular, such a solubilizate according to exemplary embodiment 4 can serve as an intermediate product for the preparation of a co-solubilizate of xanthohumol, curcumin, and glavonoid, which will be described further below.

3.8% Xantho Flay Pur-Solubilizate with Glycerol

For preparing 875 g of solubilizate. the following is used:

| | |
|---|---|
| 33.3 g | Xantho Flav Pure powder, |
| 33.3 g | glycerol 99.5%, |
| 808.4 g | polysorbate 80. |

Polysorbate 80 and glycerol are mixed by stirring while being heated to a temperature in the range from 48 to 52° C. in order to appropriately homogenize the mixture. Ethanol is incorporated into the polysorbate-glycerol mixture while stirring vigorously enough so that a homogeneous solution is obtained, while the temperature is kept constant. Then, xanthohumol is incorporated into the solution of polysorbate, glycerol, and ethanol, while the temperature is increased to a value in the range between 63 and 67° C. The stirring is performed vigorously enough so that the xanthohumol combines homogeneously with the solution.

Another option for preparing a solubilizate according to the invention is to use sucrose esters of edible fatty acids as the emulsifier.

Exemplary Embodiment 5

10% Xantho Flay Solubilizate

The following is used:

100 g Xantho-Flav powder,
598.5 g sucrose ester of edible fatty acids (E 473) "Ryoto L-1695", and
301.5 g ethanol 96% neutral alcohol type 1411U.

The sucrose ester is mixed with ethanol while stirring at room temperature in the temperature range from 20° C. to 25° C., so that a homogeneous mixture is formed, which is then heated to a maximum temperature of 80° C. while stirring. Stirring is continued until a homogeneous, transparent solution is obtained. Then the Xantho-Flav powder is added and further heated to a temperature in the range from 83° C. to 97° C. while stirring. The stirring is performed vigorously enough so that the xanthohumol combines homogeneously with the prepared solution. After having been cooled to room temperature, the solubilizate is dark brown and transparent. In this state it is bottled and then stored.

Exemplary Embodiment 6

5% Xantho Flav-Solubilizate

The following is used:

| | |
|---|---|
| 50 g | Xantho Flav powder, |
| 627 g | sucrose ester of edible fatty acids (E 473), and |
| 323 g | ethanol 96% neutral alcohol type 1411U. |

The sucrose ester of fatty acids used is a mixture comprising

| | |
|---|---|
| 41 wt. % | sucrose monolaurate, |
| 32 wt. % | sucrose monopalmitate, |
| 9 wt. % | sucrose dilaurate, |
| 8.5 wt. % | sucrose dipalmitate, |
| 7 wt. % | sucrose monostearate, and |
| 2.5 wt. % | sucrose distearate. |

This sucrose ester is mixed with ethanol while stirring at room temperature in the temperature range from 20° C. to 25° C., so that a homogeneous mixture is obtained. It may be slightly heated to a temperature in the range from 48° C. to 52° C. Stirring is continued until a homogeneous mixture or solution is obtained. Then, the Xantho-Flav powder is added and further heated to a temperature in the range from 83° C. to 97° C. while stirring. The stirring is performed vigorously enough so that the xanthohumol combines homogeneously with the prepared solution. After having been cooled to room temperature, the solubilizate is dark brown and transparent. In this state it is bottled and then stored.

Exemplary Embodiment 7

5% Xantho Flav-Solubilizate

The following is used:

| | |
|---|---|
| 50 g | Xantho Flav powder, |
| 313.5 g | sucrose ester of edible fatty acids (E 473) "Ryoto L-1695", |
| 313.5 g | sucrose ester of edible fatty acids (E 473) "Ryoto P-1670", and |
| 323 g | ethanol 96% neutral alcohol type 1411U. |

The two powdery sucrose esters are added together. Mixing is not required for this step. The sucrose esters are then mixed with ethanol at room temperature in the temperature range from 20° C. to 25° C. included, while stirring so that a homogeneous mixture is formed. The latter is heated to a maximum temperature of 80° C. while stirring. Stirring is continued until a homogeneous, transparent solution is obtained. Then the Xantho-Flav powder is added and heated to a temperature in the range from 83° C. to 97° C. while stirring. The stirring is performed vigorously enough so that xanthohumol combines homogeneously with the solution. After having been cooled to room temperature, the solubilizate is dark brown and transparent. In this state it is bottled and then stored.

Exemplary Embodiment 8

5% Xantho Flav-Solubilizate

The following is used:

| | |
|---|---|
| 50 g | Xantho Flav powder, |
| 613.75 g | sucrose ester of edible fatty acids (E 473) "Ryoto L-1695", |
| 318.25 g | ethanol 96% neutral alcohol type 1411U. |

The preparation of the solubilizate corresponds to the procedure described in exemplary embodiment 7, with one sucrose ester alone instead of the two used there.

Exemplary Embodiment 9

5% Xantho Flav-Solubilizate

The following is used:

| | |
|---|---|
| 50 g | Xantho Flav powder, |
| 142.5 g | sucrose ester of edible fatty acids (E 473) "Ryoto L-1695", |
| 332.5 g | sucrose ester of edible fatty acids (E 473) "DUB SE 16 P", |
| 304 g | ethanol 96% neutral alcohol type 1411U, and |
| 171 g | glycerol. |

The two powdery sucrose esters are combined. Mixing is not required for this step. The sucrose esters are then mixed with ethanol and glycerol at room temperature in the temperature range from 20° C. to 25° C. included, while stirring vigorously so that a homogeneous mixture is formed. The latter is heated to a maximum temperature of 80° C. while stirring. Stirring is continued until a homogeneous, transparent solution is obtained. Then the Xantho-Flav powder is added and heated to a temperature in the range from 83° C. to 97° C. while stirring. The stirring is performed vigorously enough so that the xanthohumol combines homogeneously with the solution. After having been cooled to room temperature, the solubilizate is dark brown and transparent. In this state it is bottled and then stored.

Exemplary Embodiment 10

5% Xantho Flav-Solubilizate

The following is used:

| | |
|---|---|
| 50 g | Xantho Flav powder, |
| 71.25 g | sucrose ester of edible fatty acids (E 473) "Ryoto L-1695", |
| 166.25 g | sucrose ester of edible fatty acids (E 473) "DUB SE 16 P", |
| 475 g | polysorbate 80, |
| 152 g | ethanol 96% neutral alcohol type 1411U, and |
| 82.5 g | glycerol. |

The sucrose esters are mixed with polysorbate 80, ethanol and glycerol at room temperature in the temperature range from 20° C. to 25° C. included, while stirring so that a homogeneous mixture is formed. It may be slightly heated to a temperature in the range from 48° C. to 52° C. Stirring is continued until a homogeneous mixture or solution is obtained. Then the Xantho-Flav powder is added and heated to a temperature in the range from 83° C. to 97° C. while stirring. The stirring is performed vigorously enough so that xanthohumol combines homogeneously with the prepared solution. After having been cooled to room temperature, the solubilizate is dark brown and transparent.

Exemplary Embodiment 11

5% Xantho Flav-Solubilizate

The following is used:

| | |
|---|---|
| 50 g | Xantho Flav powder, |
| 313.5 g | sucrose ester of edible fatty acids (E 473) "Ryoto M-1695", |
| 313.5 g | sucrose ester of edible fatty acids (E 473) "Ryoto P-1670", |
| 9.5 g | lecithin as a phospholipid, and |
| 313.5 g | ethanol 96% neutral alcohol type 1411U. |

The two powdery sucrose esters are combined. Mixing is not required for this step. The lecithin is mixed with ethanol. It can be slightly heated to a temperature in the range from 40° C. to 50° C. The sucrose ester mixture is then mixed with the mixture of ethanol and lecithin at room temperature in the temperature range from 20° C. to 25° C. included, while stirring vigorously enough so that a homogeneous mixture is formed. If necessary, it can be slightly heated to a temperature in the range from 40° C. to 50° C. This can also be achieved by adding the previously heated ethanol-lecithin mixture. The mixture is heated to a maximum temperature of 80° C. while stirring. Stirring is continued until a homogeneous, transparent solution is obtained. Then, the Xantho-Flav powder is added and heated to a temperature in the range from 83° C. to 97° C. while stirring. The stirring is performed vigorously enough so that the Xantho Flav powder, i.e. the xanthohumol, combines homogeneously with the prepared solution. After having been cooled to room temperature, the solubilizate is dark brown and transparent. In this state it is bottled and then stored.

Exemplary Embodiment 12

5% Xantho Flav Solubilizate

The following is used:

| | |
|---|---|
| 50 g | Xantho Flav powder, |
| 332.5 g | sucrose ester of edible fatty acids (E 473) "Ryoto L-1695", |
| 142.5 g | sucrose ester of edible fatty acids (E 473) "DUB SE 16 P", |
| 152 g | ethanol 96% neutral alcohol type 1411U, |
| 85.5 g | glycerol, and |
| 237.5 g | water. |

The two powdery sucrose esters are combined. Mixing is not required for this step. The sucrose esters are then mixed with ethanol, water and glycerol at room temperature in the temperature range from 20° C. to 25° C. included, while stirring vigorously so that a homogeneous mixture is formed. The latter is heated to a maximum temperature of 80° C. while stirring. Stirring is continued until a homogeneous, transparent solution is obtained. Then, the Xantho-Flav powder is added and heated to a temperature in the range from 83° C. to 97° C. while stirring. The stirring is performed vigorously enough so that xanthohumol combines homogeneously with the prepared solution. After having been cooled to room temperature, the solubilizate is dark brown and transparent. In this state it is bottled and then stored.

Exemplary Embodiment 13

10% Xantho Flav-Solubilizate

The following was used:

| | |
|---|---|
| 100 g | Xantho-Flav powder, |
| 315 g | sucrose ester of edible fatty acids (E 473) "Ryoto L-1695", |
| 135 g | sucrose ester of edible fatty acids (E 473) "DUB SE 16 P", |
| 144 g | ethanol 96% neutral alcohol type 1411U, |
| 81 g | glycerol, and |
| 225 g | water. |

The preparation of the solubilizate corresponds to the procedure described in exemplary embodiment 12.

Another option for preparing a solubilizate according to the invention is a combined solubilizate comprising xanthohumol and curcumin.

Exemplary Embodiment 14

Solubilizate of 5% Xantho Flav Pur/3% Curcumin

The following is used:

| | |
|---|---|
| 50 g | Xantho-Flav Pur powder, |
| 37.5 g | 95% curcumin powder, |
| 75 g | ethanol 96% neutral alcohol type 1411U, and |
| 837.5 g | polysorbate 80. |

The polysorbate is heated to a temperature in the range between 48 and 52° C., then the curcumin powder is incorporated while heating to a value in the range between 58 and 62° C. The stirring is performed vigorously enough so that the curcumin powder is evenly drawn into the polysorbate and a homogeneous solubilizate is formed. Ethanol is then dissolved in the curcumin solubilizate while keeping constant the temperature. Then, the Xantho-Flav Pur powder is added. The stirring is performed vigorously enough so that the Xantho-Flav Pur powder is evenly drawn into the ethanol-containing curcumin solubilizate and a homogeneous co-solubilizate is formed. While adding the Xantho-Flav Pure powder, the temperature is increased to a value in the range from 85 to 89° C. After having been cooled to a maximum temperature of 45° C., the co-solubilizate is bottled while being stirred and is stored in the dark at temperatures below 25° C.

For a particle size analysis of the solubilizate as described under exemplary embodiment 14, this solubilizate was first diluted with distilled water in a ratio of 1:500 and brought to 37° C. under continuous stirring using a magnetic stirrer and a hot plate.

Subsequently, the pH was adjusted to 1.1 using 32% hydrochloric acid. The samples were then immediately measured. The results are compiled in the table below, for which the data from two measurements were averaged.

|  | $d_{10}$ (nm) | $d_{50}$ (nm) | $d_{90}$ (nm) | $d_{99}$ (nm) |
|---|---|---|---|---|
| Intensity distribution | 10.72 | 18.15 | 468.24 | 933.00 |
| Volume distribution | 6.90 | 10.78 | 16.14 | 22.17 |

Such a direct preparation can also be employed to prepare co-solubilizates of xanthohumol and curcumin which have a higher load of active substances. One example for this is described below.

Exemplary Embodiment 15

Solubilizate of 6.3% Xantho Flay Pur/4% Curcumin

The following is used:

| | |
|---|---|
| 63 g | Xantho-Flav Pur powder, |
| 43 g | curcumin powder 95%, |
| 84 g | ethanol 96% neutral alcohol type 1411U, and |
| 810 g | polysorbate 80. |

The polysorbate is heated to a temperature in the range between 48 and 52° C., then the curcumin powder is incorporated while heating to a value in the range between 58 and 62° C. The stirring is performed vigorously enough so that the curcumin powder is evenly drawn into the polysorbate and a homogeneous solubilizate is formed. Ethanol is then dissolved in the curcumin solubilizate at a constant temperature. Then the Xantho-Flay Pur powder is added. The stirring is performed vigorously enough so that the Xantho-Flav Pure powder is evenly drawn into the ethanol-containing curcumin solubilizate and a homogeneous co-solubilizate is formed. While adding the Xantho-Flay Pur powder, the temperature is increased to a value in the range from 85 to 89° C. After cooling to a maximum temperature of 45° C., the co-solubilizate is bottled while being stirred and is stored in the dark at temperatures below 25° C.

Exemplary Embodiment 16

Furthermore, a solubilizate according to the invention may also be obtained as a combined solubilizate comprising xanthohumol and glavonoid.

Solubilizate of 5% Xantho Flay Pure/7.5% Glavonoid (=2.25% Glabridin)

The following is used:

| | |
|---|---|
| 50 g | Xantho-Flav Pure powder, |
| 75 g | Kaneka glavonoid (3% glabridin) = 2.25 g glabridin, |
| 75 g | ethanol (96%) neutral alcohol type 1411U, |
| 50 g | glycerol 99.5%, and |
| 750 g | polysorbate 80. |

First, polysorbate 80 and glycerol are mixed and heated to a temperature in the range between 48 and 52° C. while stirring. Ethanol is added to this fluid, stirring is performed vigorously enough so that the fluids combine homogeneously with each other at a constant temperature. Xanthohumol, i.e. Xantho-Flav Pur powder, is added while further heating to a temperature in the range between 63 and 67° C. Similar to the subsequent addition of the glavonoid, the stirring is performed vigorously enough so that the fluids combine homogeneously with each other. Glavonoid is added while increasing the temperature to a value in the range between 85 and 89° C. The resulting co-solubilizate containing xanthohumol and glavonoid is cooled to a maximum temperature of 45° C. while stirring and is then bottled.

Turbidity measurements were made with a dilution in water of 1:500 at a pH of 1.1 and a temperature of 37° C., i.e. under physiological conditions. The value averaged over two samples is 0.6 FNU, which is calculated from individual values 0.6 FNU and 0.6 FNU.

For particle size analysis, this solubilizate was first diluted with distilled water in a ratio of 1:500 and brought to 37° C. under constant stirring using a magnetic stirrer and a hot plate. Subsequently, the pH was adjusted to 1.1 using 32% hydrochloric acid. The samples were then measured immediately. The results are compiled in the table below.

|  | $d_{10}$ (nm) | $d_{50}$ (nm) | $d_{90}$ (nm) | $d_{99}$ (nm) |
|---|---|---|---|---|
| Intensity distribution | 8.66 | 11.83 | 16.23 | 21.03 |
| Volume distribution | 7.25 | 9.92 | 13.52 | 17.46 |

Exemplary Embodiment 17

A co-solubilizate comprising xanthohumol and glavonoid can also be prepared without ethanol.

Solubilizate of 6.3% Xantho Flay Pur/9% Glavonoid (=2.7% Glabridin)

The following is used:

| | |
|---|---|
| 63 g | Xantho-Flav Pur powder, |
| 90 g | Kaneka Glavonoid (3% Glabridin) = 2.25 g glabridin, |
| 90 g | glycerol 99.5%, and |
| 757 g | polysorbate 80. |

First, polysorbate 80 and glycerol are mixed and heated to a temperature in the range between 48 and 52° C. while stirring. Xanthohumol is added while further heating to a temperature in the range between 63 and 67° C. Similar to the subsequent addition of the glavonoid, the stirring is performed vigorously enough so that the fluids combine homogeneously with each other. Glavonoid is added while increasing the temperature to a value in the range between 85 and 89° C. The resulting co-solubilizate containing xanthohumol and glavonoid is cooled to a maximum temperature of 45° C. while stirring and is bottled.

A further variant of the solubilizate according to the invention is a xanthohumol solubilizate which additionally contains curcumin and glavonoid. Such solubilizates are described in exemplary examples 18 and 19.

Exemplary Embodiment 18

Solubilizate of 2.4% Curcumin/3.3% Xantho-Flav Pur/5% Glavonoid (=1.5% Glabridin)

The following is used:

| | |
|---|---|
| 25 g | curcumin powder 95% (=23.75 curcumin), |
| 33.3 g | Xantho-Flav Pur powder, |

-continued

| | |
|---|---|
| 50 g | Kaneka glavonoid (3% glabridin) (=1.5 g glabridin), |
| 50 g | ethanol 96% neutral alcohol type 1411U, |
| 33.3 g | glycerol 99.5%, |
| 808.4 g | polysorbate 80. |

Polysorbate 80 and glycerol are mixed together under stirring while being heated to a temperature in the range from 48 to 52° C. to adequately homogenize the mixture. Ethanol is incorporated into the polysorbate-glycerol mixture while stirring vigorously enough to obtain a homogeneous solution, while the temperature is kept constant. Then, xanthohumol is incorporated into the solution of polysorbate, glycerol, and ethanol, while the temperature is raised to a value between 63 and 67° C. while stirring vigorously enough for the xanthohumol to combine homogeneously with the prepared solution.

Subsequently, curcumin powder is incorporated into the xanthohumol solubilizate, while raising the temperature to a value in the range between 78 and 82° C. As with the xanthohumol and also similar to the incorporation of glavonoid described below, stirring is performed vigorously enough so that the newly added component of the solubilizate combines homogeneously with the solubilized product in the prepared fluid. For the addition of glavonoid, the temperature is further increased to a value in the range between 85 and 98° C.

The product is a solubilizate with co-micellized curcumin, xanthohumol, and glavonoid. It is allowed to cool down to a maximum value of 45° C. while stirring and is then bottled.

For a particle size analysis of the solubilizate described under exemplary embodiment 18, this solubilizate was first diluted with distilled water in a ratio of 1:500 and brought to 37° C. under constant stirring using a magnetic stirrer and a hot plate. Then, the pH was adjusted to 1.1 using 32% hydrochloric acid. The samples were then immediately measured. The results are compiled in the table below, for which data from two measurements were averaged.

| | $d_{10}$ (nm) | $d_{50}$ (nm) | $d_{90}$ (nm) | $d_{99}$ (nm) |
|---|---|---|---|---|
| Intensity distribution | 4.94 | 16.20 | 627 | 1729 |
| Volume distribution | 3.49 | 4.93 | 11.89 | 16.13 |

Exemplary Embodiment 19

Solubilizate of 3% Curcumin/4.4% Xantho-Flav Pur/5% Glavonoid (=1.8% Glabridin)

The following is used:

| | |
|---|---|
| 32 g | curcumin powder 95% (=30.4 g curcumin), |
| 44 g | Xantho-Flav Pur powder, |
| 60 g | Kaneka glavonoid (=1.8 g glabridin), |
| 60 g | ethanol 96% neutral alcohol type 1411U, |
| 44 g | glycerol 99.5%, |
| 760 g | polysorbate 80. |

This solubilizate is prepared in the same way as the solubilizate described above with 2% curcumin, 3.3% Xantho-Flav Pur, and 5% glavonoid.

For the co-solubilizate described first, turbidity measurements were made with a dilution in water in a ratio of 1:500 under physiological conditions of pH=1.1 and a temperature of 37° C. As a result thereof, the value of turbidity for the aqueous dilution of the solubilizate was found to be 1.3 FNU, which is an averaged value from two measurements (2.5 FNU; 0.6 FNU).

A verification about whether the homogenization of the components to form a solubilizate according to the invention has been sufficiently completed is obtained by measurements of the clarity of the product using a laser beam. Such a laser beam measurement may be performed, for example, by illuminating the sample using a commercially available laser pointer, in particular with a wavelength in the range between 650 nm and 1700 nm (red spectral color), and subsequent visual inspection of the illuminated or irradiated solubilizate. The verification is not achieved by sampling, i.e. outside the reaction vessel, but rather in the reaction vessel. The laser beam is directed perpendicular to the reaction vessel through a sight glass which is located on the front of the reaction vessel. If merely a point of light appears on the rear inner surface of the reaction vessel, completely free of scattering, this means that the resulting particle structures in the reaction vessel are smaller than the wavelength of the visible light, which is thus a visual confirmation that the process of micellization has been completed.

Advantageously, the small particle sizes as measured imply that a liquid has been formed that is particularly clear for the human eye.

The clarity of the solubilizate can also be demonstrated by its low turbidity. For this purpose, the following working hypothesis is applied: The clearer an aqueous dilution of a solubilizate or of another formulation of xanthohumol or of a combination of xanthohumol with glavonoid and/or curcumin, especially under physiological conditions of a gastric passage, i.e. at a pH of 1.1 and a temperature of 37° C., the better its solubilization. The better the solubilization, the better is the bioavailability of the active substance or of the product containing it.

This can already be deduced from the particularly low turbidity of the solubilizate, which can be considered as a kind of parameter for bioavailability. The turbidity of the solubilizates according to the invention was determined by scattered light measurement using infrared light according to the specifications of the ISO 7027 standard.

Without additives as in soft and hard gelatin capsules, the inventive transparent and completely stable water-soluble formulation exhibits pH-independent stable transparency in gelatin-free capsules (hard and/or soft) and in water-based liquid end products. Products with such transparency and water solubility are urgently sought by the relevant industry for innovative products as a capsule filling. To the knowledge of the inventor, a xanthohumol formulation which meets these requirements does not yet exist.

With the inventive formulation in a solubilizate that includes very small, stable and gastro-resistant micelles, the invention provides a xanthohumol solubilizate for use as a dietary supplement and/or pharmaceutical drug, in particular for use as a dietary supplement and/or pharmaceutical drug for the treatment of obesity.

In the context of the invention, the amounts of xanthohumol and optionally of curcumin in the individual solubilizates can also be adjusted to be significantly higher than in the presented example, depending on the application case.

When adjusting higher loads of active substance, this is limited by the fact that when exceeding an amount of active substance that is individual for the respective composition, no solubilizate will be produced any more but rather an emulsion. When the content of active substance is increased, the respective contents of the other components (in wt. %)

necessarily decrease. Beyond a specific threshold, a disperse system will be obtained which, however, is not irreversibly soluble in water like the solubilizates of the invention and does not have the very low turbidity measured for these solubilizates under physiological conditions of the gastric passage, i.e. at pH 1.1 and 37° C. Such dispersions may be (nano)emulsions, but they do not constitute solubilizates in which the active substance(s) are enclosed in the very small micelles. However, according to the inventor's experience, only the solubilizates provide for the significantly enhanced bioavailability of the active substance or active substances according to the invention, even if an emulsion allowed for a higher load of active substance.

The medical faculty of Friedrich-Alexander University Erlangen Nürnberg (FAU) conducted studies on the effects of xanthohumol on body weight. A dose of 2.5 mg/kg body weight of xanthohumol was administered daily. For this purpose, a solubilizate of the present Applicant was used. It was prepared from 100 g "Xantho-Flav Pure", 150 g of 96% ethanol, and 750 g of polysorbate 80. For adjusting the concentration to 0.375 mg/ml, the solubilizate was diluted with double-distilled water ("ddH$_2$O"). The corresponding data are marked by "s-XN" in the accompanying figures.

For comparison, similar experiments were conducted with the same dose of native xanthohumol. For dissolving the native xanthohumol, an aqueous solution of methylhydroxypropyl cellulose (MHPC, 0.2%, Methocel E4M Premium CR, Hypromellose 2910 USP, Fragron Inc., Minnesota, USA) was used. The corresponding data are marked by "n-XN".

The solutions were freshly prepared each week and stored in a cool place protected from light.

Male mice of the strain C57BL/6 at an age of 8 weeks either received usual diet or were fed according to the "Western type diet" consisting of 15% pork lard, 15% beef tallow, 4% palmitic acid, 4% stearic acid, 0.2% cholesterol, and 30% sucrose. The control group (CTRL), which received the usual diet, was given an aqueous solution of methylhydroxypropyl cellulose (MHPC, 0.2%, Methocel™ E4M prem) ("vehicle" VH) as a therapy, as was the case with the "Western type diet" group ("WTD").

Other groups received the xanthohumol solubilizate ("s-XN") of the present Applicant or native xanthohumol ("n-XN") in addition to the WTD. The therapy was conducted over 8 weeks.

After seven weeks of administration of the solubilizate or of native xanthohumol, an intraperitoneal glucose tolerance test (ipGTT) was carried out. After 12 hours of fasting, the mice were injected intraperitoneally with a glucose solution in a glucose concentration of 50% (mass of glucose per volume) in a dose of 3 mg of glucose per gram of body weight. The concentration of glucose in the blood was measured in samples that were taken from the tail vein prior to glucose administration (fasting glucose) as well as 30, 60, 80, and 120 minutes thereafter. The measurement was performed using a glucometer of the "accutrend" model (Roche, Mannheim, Germany).

To quantify liver lipids, the latter were extracted and the amount of triglycerides ("hepatic triglyceride level") was determined using a "GPO-triglyceride kit" (Sigma, Deisenhofen, Germany), as described in Wobser et al.: "Lipid accumulation in hepatocytes induces fibrogenic activation of hepatic stellate cells", Cell Res 2009; 19:996-1005.

RNA isolation from liver tissue, reverse transcription and quantitative real-time polymerase chain reaction (PCR) analysis were carried out using the "LightCycler" technology (Roche) and specific tests for primers, as described in Hellebrand et al.: "Promoter hypermethylation is causing functional relevant downregulation of methylthioadenosine phosphorylase (MTAP) expression in hepatocellular carcinoma", Carcinogenesis 2006; 27:64-72.

For histological analysis, liver tissue samples from the mice were fixed in 4% formalin at room temperature for 24 hours, dried in ascending ethanol series and embedded in paraffin. Sections of these formalin-fixed tissue blocks with a thickness of 5 micrometers were deparaffinized using xylene and stained using hematoxylin and eosin, as described in Dorn et al.: "Increased expression of c-Jun in nonalcoholic fatty liver disease", Lab Invest. 2014; 94:394-408.

Figure 1D:
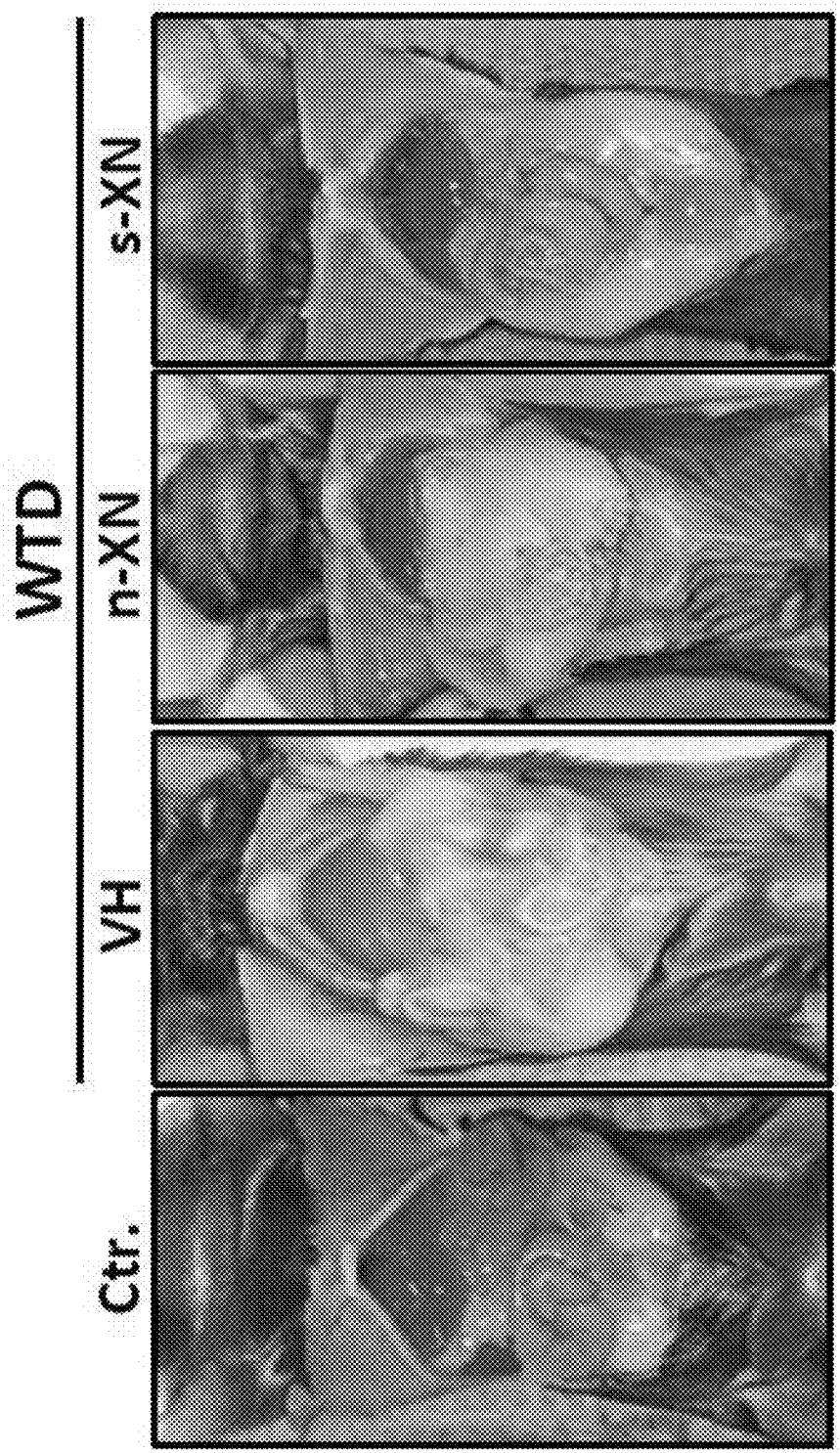
FIG. 1D is a photograph of test animals.
Figure 1E:
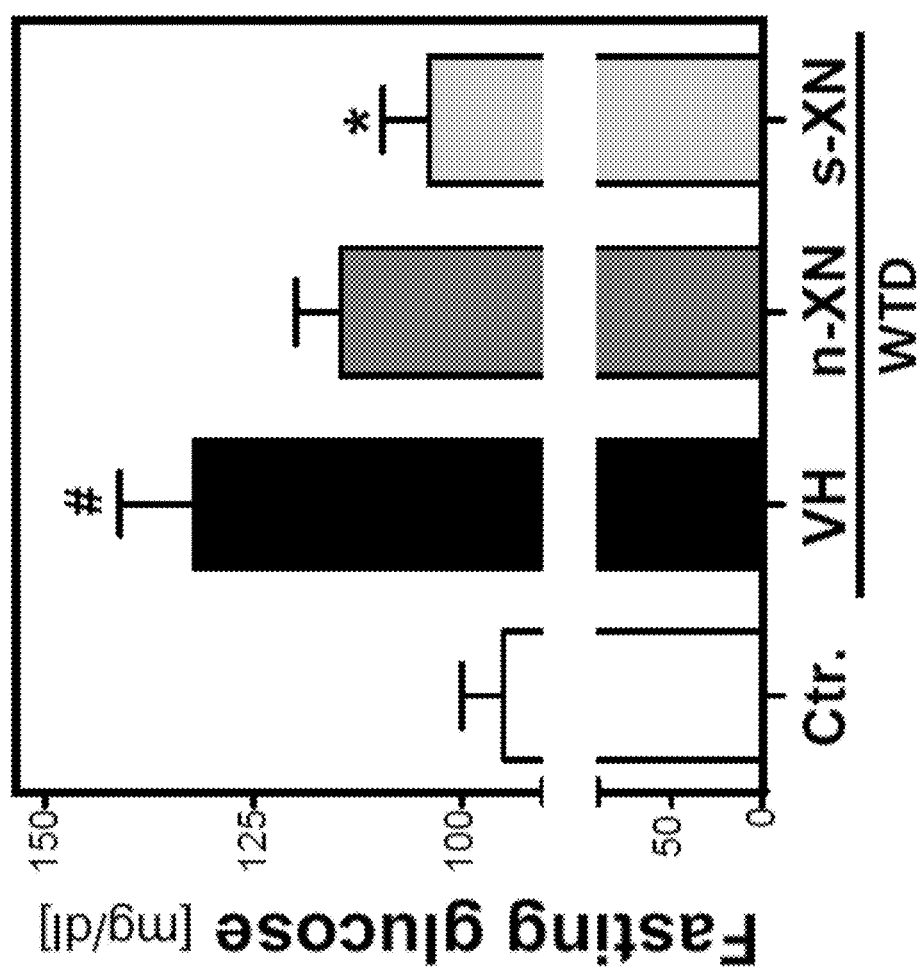
FIG. 1E is a graph showing effects on fasting glucose and glucose tolerance.
Figure 1F:
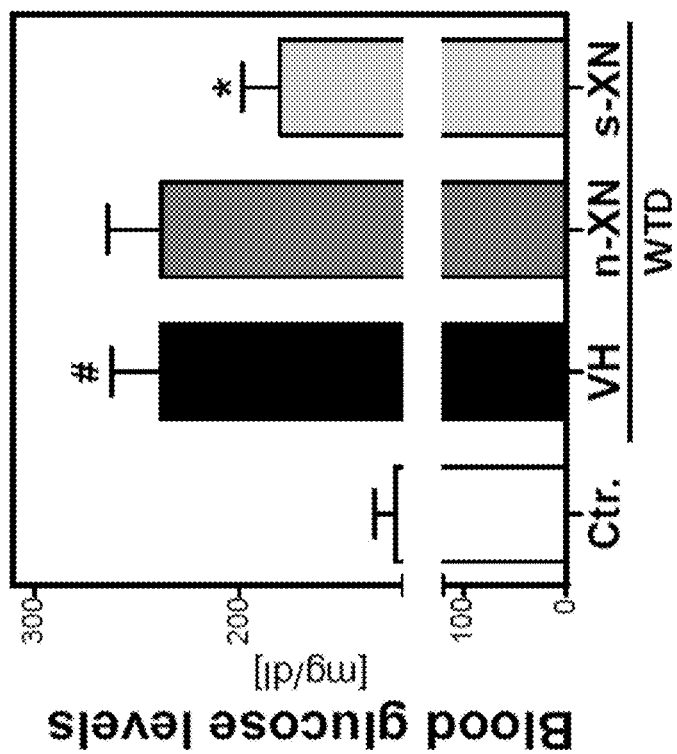
FIG. 1F is a graph showing effects on fasting glucose and glucose tolerance.
Figure 1F:
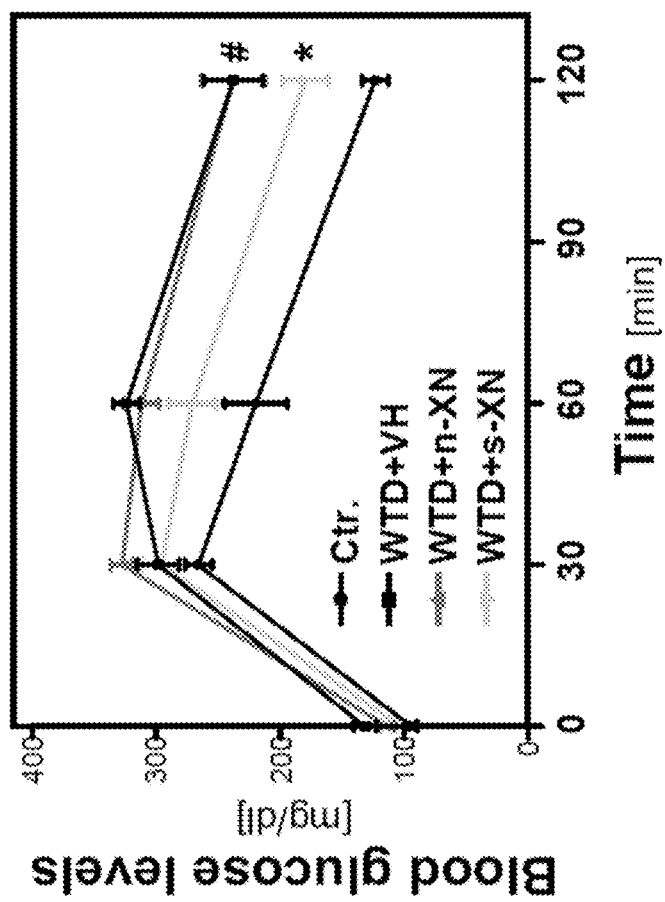

The results of the experiments discussed above are illustrated in the graphs of the accompanying figures, wherein:

FIGS. 1A to 1D
show effects on weight gain and (visceral) fat accumulation when xanthohumol solubilizate (s-XN) or native xanthohumol (n-XN) is administered during WTD diet;

FIGS. 1E and 1F show effects on fasting glucose and glucose tolerance when xanthohumol solubilizate (s-XN) or native xanthohumol (n-XN) is administered during WTD nutrition;

FIG. 2 shows effects on steatosis, liver weight, and on the amount of triglyceride in the liver when xanthohumol solubilizate (s-XN) or native xanthohumol (n-XN) is administered during WTD diet;

FIG. 3 shows effects on the release of liver fibrosis-provoking genes in the liver (hepatic expression of pro-fibrogenetic genes) when xanthohumol solubilizate (s-XN) or native xanthohumol (n-XN) is administered during WTD diet; and FIG. 4 shows effects on the release of liver cirrhosis-triggering proteins when xanthohumol solubilizate (s-XN) or native xanthohumol (n-XN) is administered during WTD diet.

The indication "*" in the figures means p<0.05 in comparison to the data for the "therapy" with the vehicle (VH). The indication "#" in the figures means p<0.05 in comparison to the data for the control group (CTR).

Figure 5:
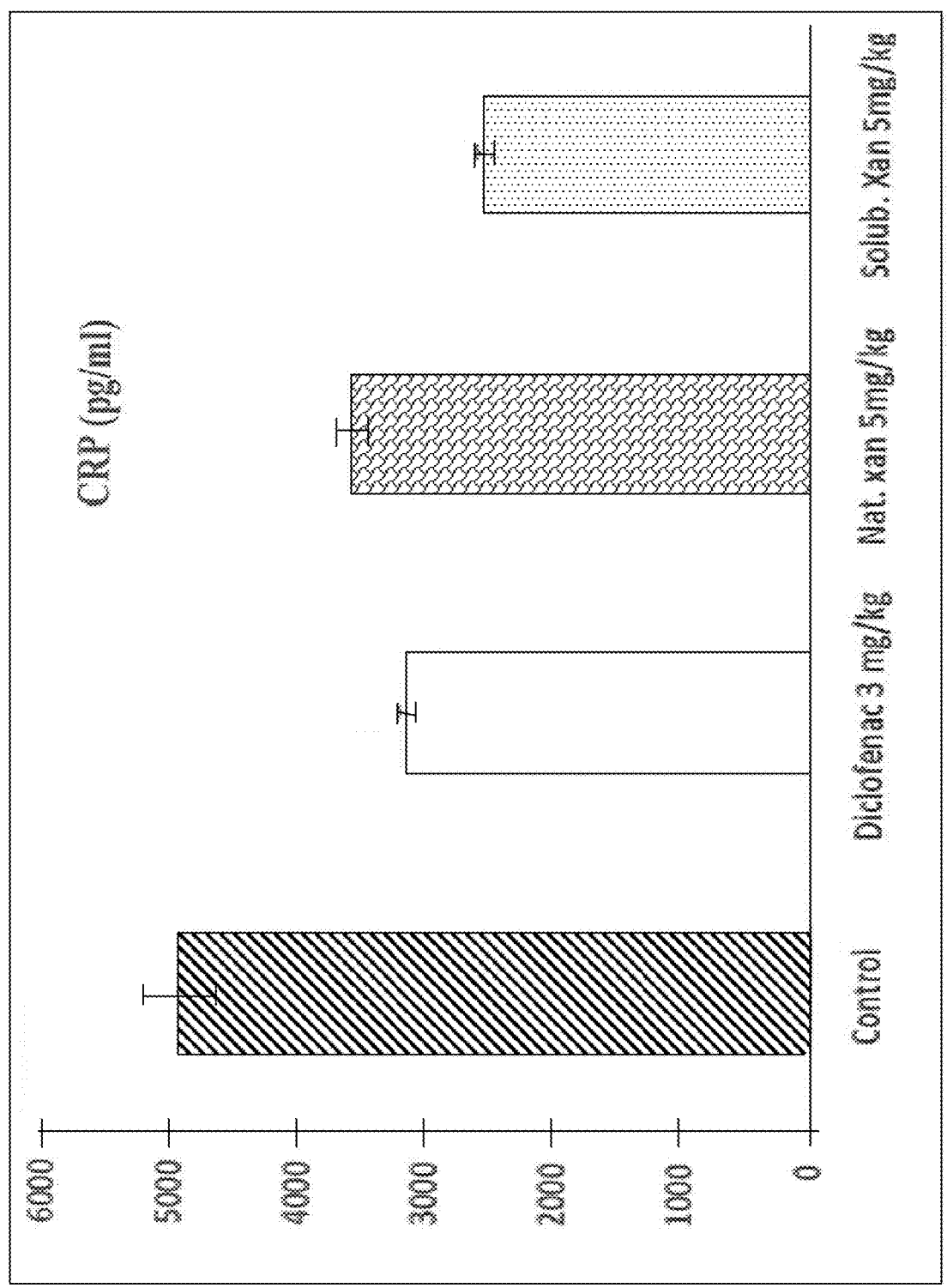
FIG. 5 is a graph that shows the effect of xanthohumol in native and in solubilized form on the CRP serum level (pg/l).
Figure 6:
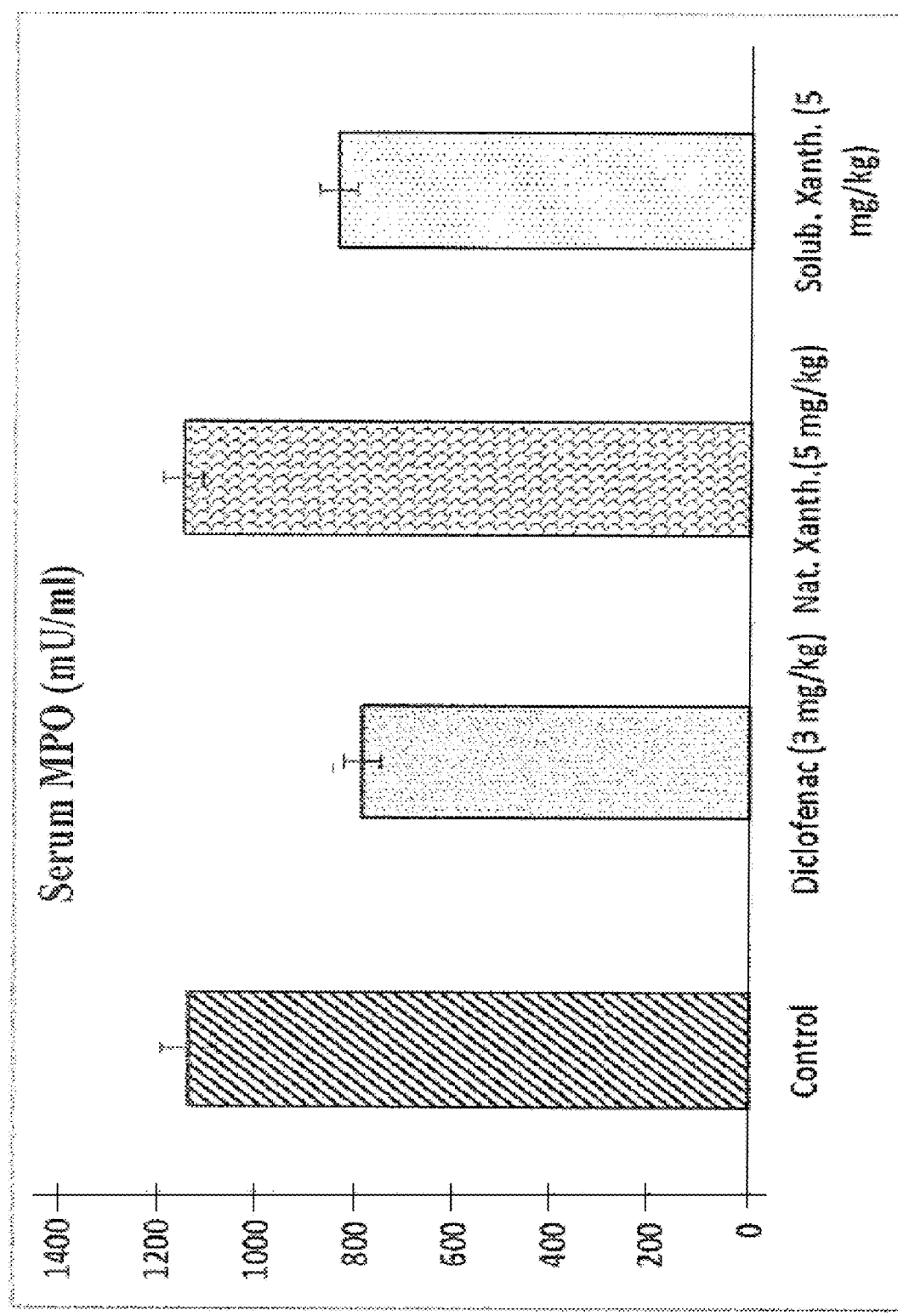
FIG. 6 is a graph that shows the effect of xanthohumol in native and in solubilized form on the MPO serum level (mU/ml).

Prof. Dr. M. T. Khayyal from the University of Cairo, Faculty of Pharmacy at the Institute for Pharmacology, performed further studies on the anti-inflammatory effect of xanthohumol, also in combination with curcumin, in each case in the native form and in the solubilized form according to the invention. The results of these studies are illustrated in the graphs of the following figures, wherein:

FIG. 5 shows the effect of xanthohumol in native and in solubilized form on the CRP serum level (pg/l); and FIG. 6 shows the effect of xanthohumol in native and in solubilized form on the MPO serum level (mU/ml).

WTD not only caused weight gain (FIG. 1A), but also a significant increase in the mass of visceral and subcutaneous adipose tissue. Photographs of the laboratory animals according to FIGS. 1C and 1D show that the administration of the xanthohumol solubilizate caused a reduction in the mass of visceral fat.

Feeding with WTD also led to a higher fasting glucose value and reduced glucose tolerance compared with mice which were fed with the control, which indicates insulin resistance (cf. FIGS. 1E and 1F). The administration of the xanthohumol solubilizate according to the invention caused a significant improvement in the elevated fasting glucose values and in glucose tolerance, while native xanthohumol did not bring about this effect.

As a result, the use of solubilized xanthohumol according to the invention improved the obesity and insulin resistance induced by WTD.

Figure 2A:
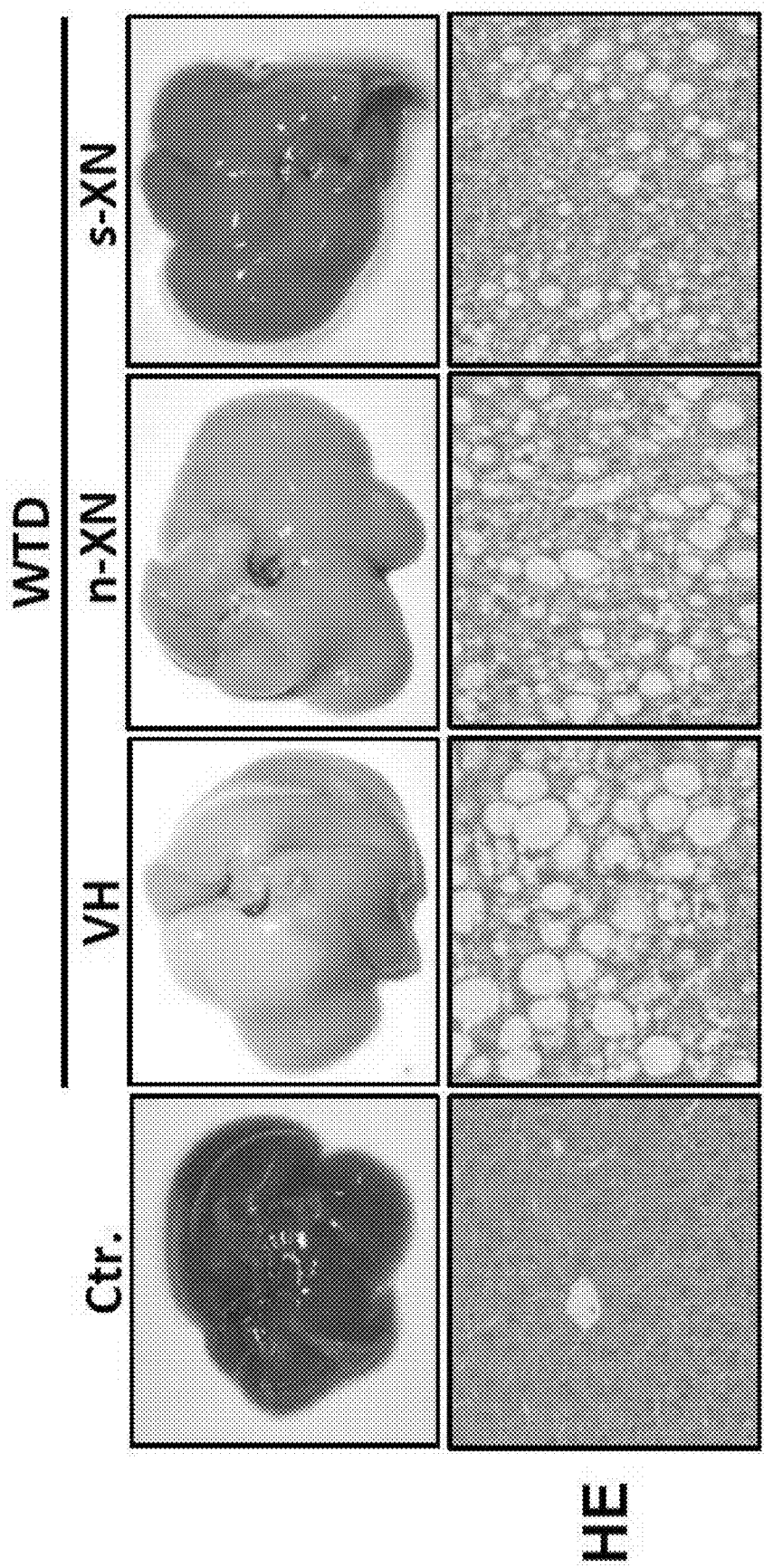
FIG. 2A shows photographs of livers of laboratory animals.
Figure 2C:
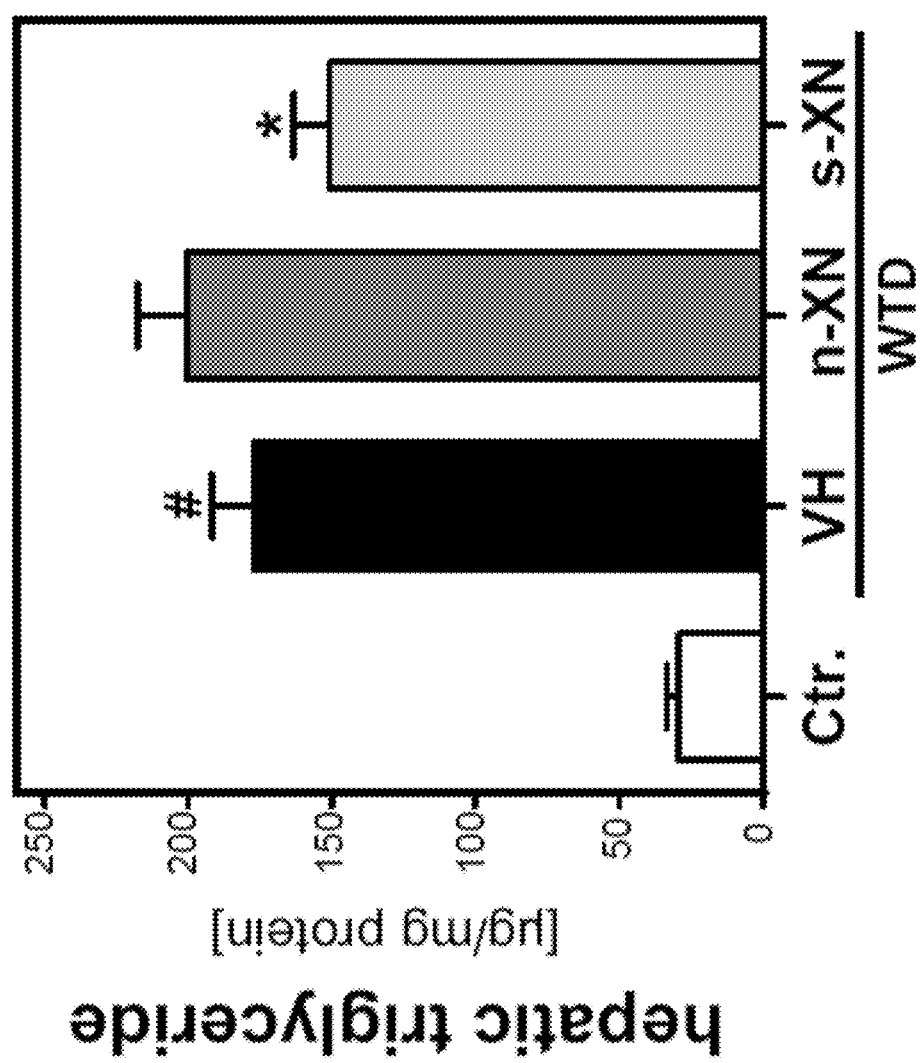
FIG. 2C is a graph showing triglyceride levels.

Furthermore, WTD caused an increase in the size of the liver of the laboratory animals, which is apparent both from the photographs of the organs that were removed from the animals at the end of the test series (FIG. 2A) and from an increase in the weight of the liver (FIG. 2B). A light color of the liver also indicates an accumulation of fat in the liver (steatosis) (FIG. 2A for administration of the vehicle and for native xanthohumol). Administration of the solubilizate according to the invention in addition to WTD almost completely reversed the increase in liver weight, that is to say resulted in almost reaching the initial value again (FIG. 2B).

WTD moreover increased the triglyceride level in the liver. Histology of the liver also confirmed the finding of fatty liver (hepatic steatosis). The administration of the xanthohumol solubilizate according to the invention in combination with WTD caused a remarkable decrease in the amount of triglycerides in the liver (FIG. 2C), which was also found in histological examinations in which only minimal steatosis was observed compared to the control group.

Figure 3B:
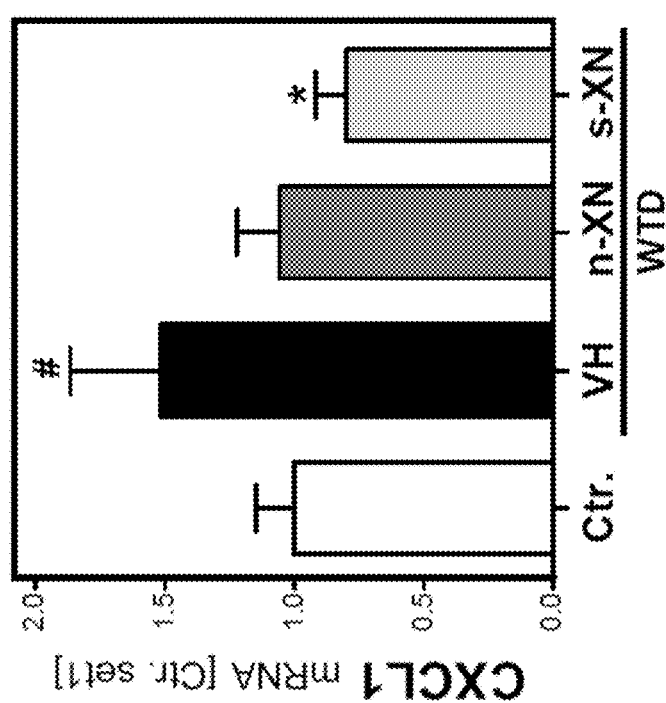
FIG. 3B is a graph showing liver inflammation markers.
Figure 3A:
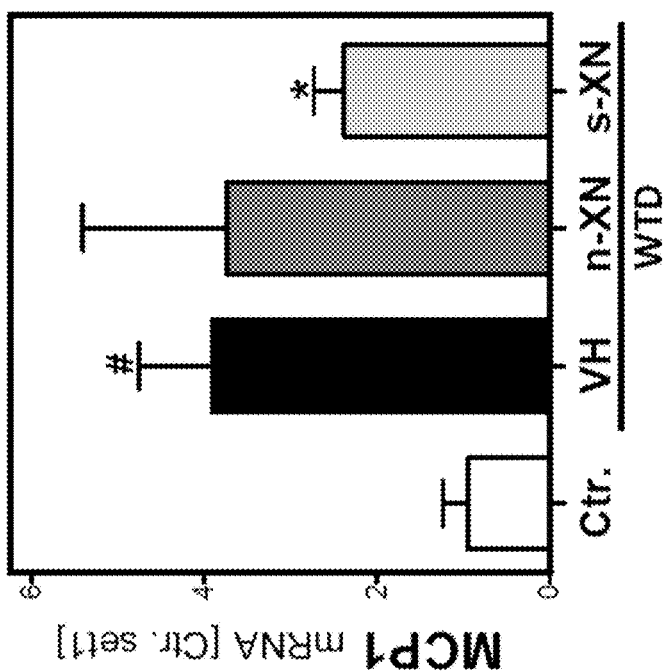
FIG. 3A is a graph showing liver inflammation markers.
Figure 3C:
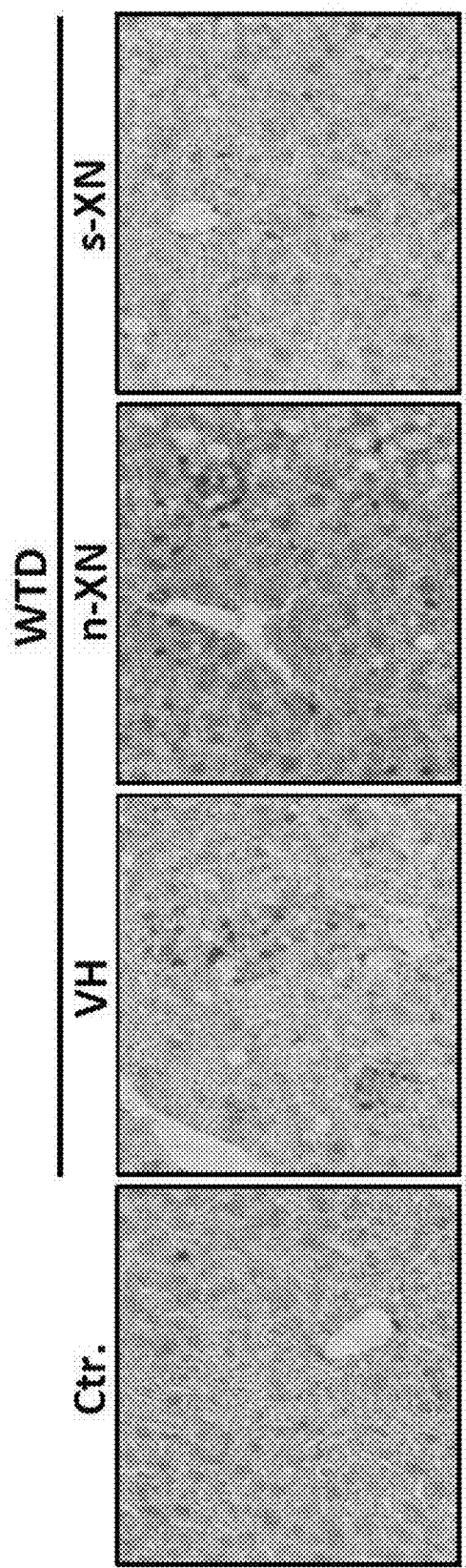
FIG. 3C is a graph and illustration showing shows effects on the release of liver fibrosis-provoking genes in the liver.
Figure 3C:
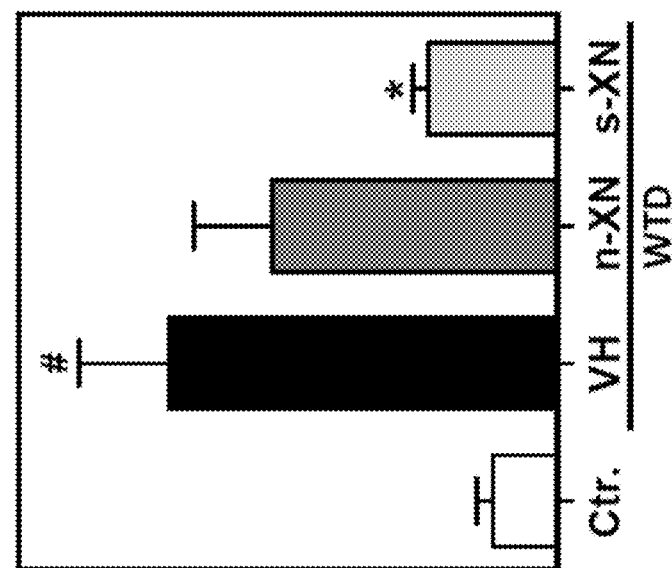

The markers of liver inflammation (expression of pro-inflammatory chemokine MCP-1 and of cytokine CXCL1) were significantly increased by the WTD compared to the control (see FIGS. 3A and 3B). The administration of the xanthohumol solubilizate of the invention in combination with WTD resulted in a significant mitigation of the increase in these two parameters (see FIG. 3A).

Figure 4A:
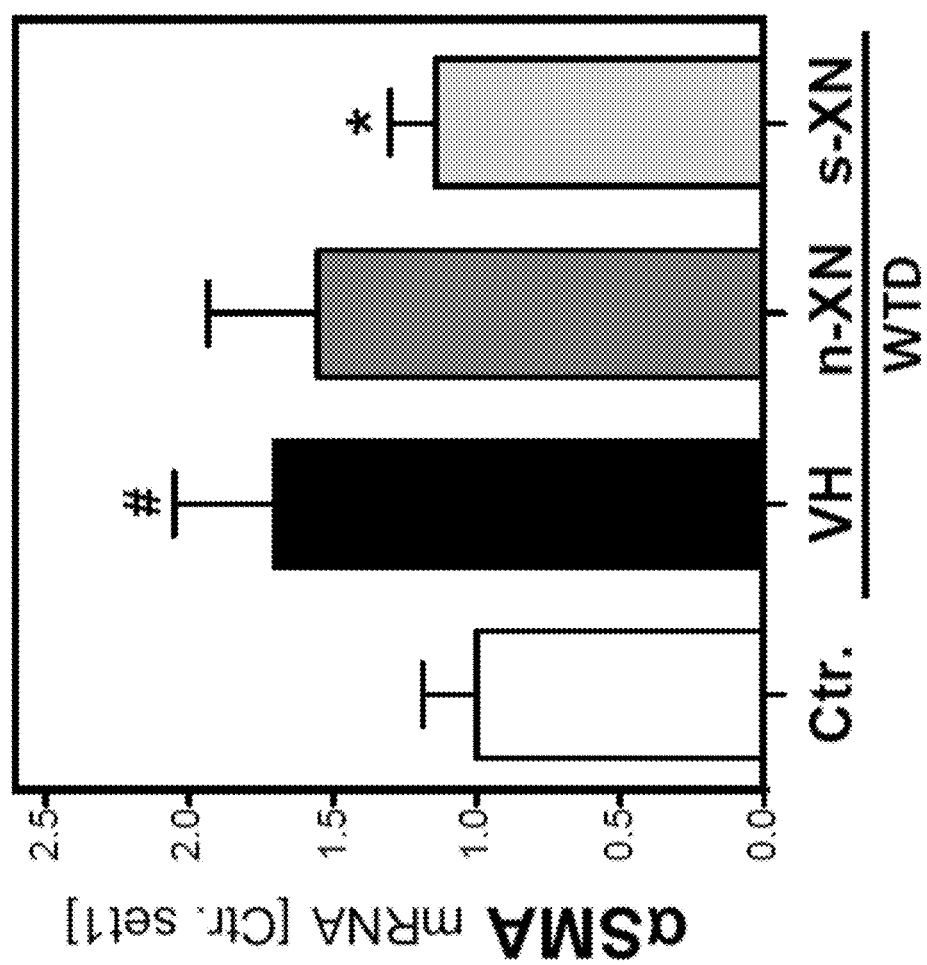
FIG. 4A is a graph showing effects on the release of liver cirrhosis-triggering proteins when xanthohumol solubilizate (s-XN) or native xanthohumol (n-XN) is administered during WTD diet.

A quantitative qPCR analysis of the livers of the WTD fed mice showed an increased expression of the alpha-smooth muscle actin ($\alpha$-SMA), a protein of the smooth muscles (cf. FIG. 4A). The $\alpha$-SMA protein is an established marker of activated hepatic stellate cells (HSC) which trigger liver cirrhosis. An immunohistochemical analysis of the $\alpha$-SMA protein confirmed that WTD causes significant activation of HSC (FIG. 4B).

Figure 4B:
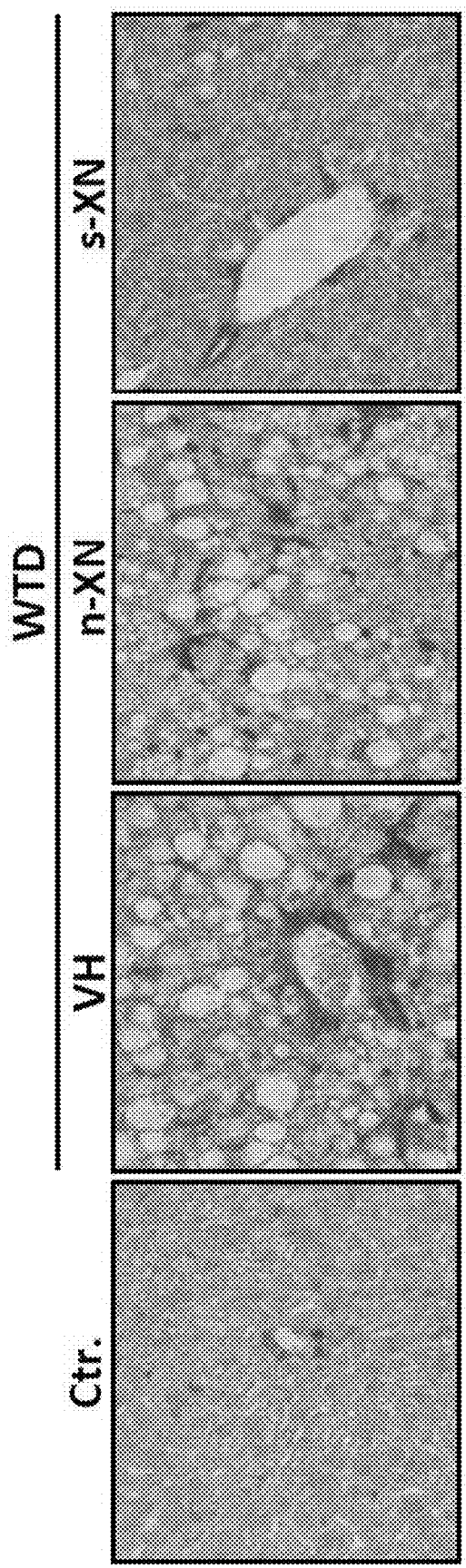
FIG. 4B shows photographs illustrating effects on the release of liver cirrhosis-triggering proteins when xanthohumol solubilizate (s-XN) or native xanthohumol (n-XN) is administered during WTD diet.
Figure 4C:
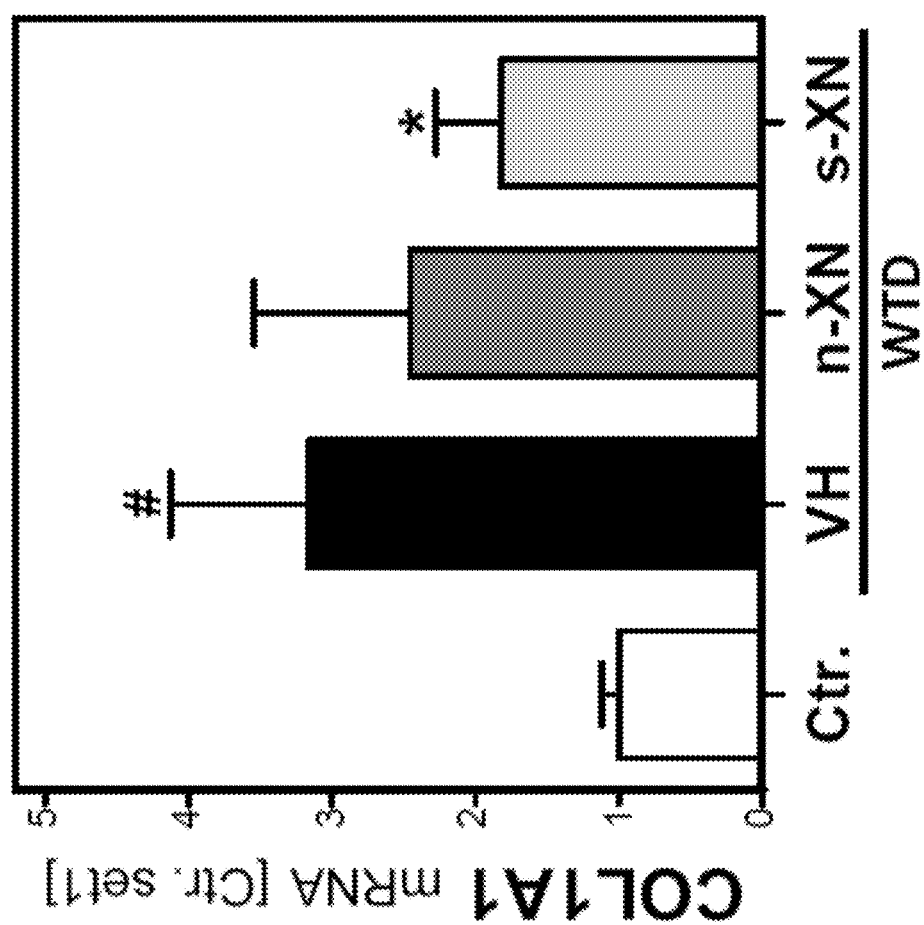
FIG. 4C is a graph showing COL1A1 levels.

This is associated with a significantly increased expression of type 1 collagen (COL1A1) in the liver of mice fed with WTD compared to the control group (FIG. 4C). Type 1 collagen (COL1A1) is the most important extracellular matrix protein in liver fibrosis, both quantitatively and qualitatively.

It is noteworthy that the treatment with the xanthohumol solubilized according to the invention significantly impedes the WTD-induced expression of $\alpha$-SMA and type 1 collagen, while native xanthohumol shows hardly any effects (FIGS. 4A, 4B, and 4C).

The solubilizate of the invention is therefore suitable for reducing an already developing liver inflammation, steatosis, and fibrosis.

These findings are particularly surprising because the xanthohumol administration with the solubilizate according to the invention was given to organisms that had already been impaired by the previous WTD diet. In biological systems or in conjunction with the examination of active substances for diseases, it is much easier to prove an effect if the active substance is administered together with the disease-inducing agent or mechanism, here the WTD, from the beginning. However, in the context of the examinations described above, the solubilizate of the invention was only administered when obesity was already manifest or when organ damage was already advanced, that is to say in the therapy phase of the experiment.

The doses for humans were calculated in correspondence to the doses determined on rats in further animal experiments as described below. The conversion of the dosage for rats into the dosage for humans, in mg per kg body weight and day in each case, is made according to the equation $$Dose_{human} = \frac{Dose_{rat}}{37} \cdot 6$$

An example for the administration of 5 mg of xanthohumol will be explained below:

148 5 mg xanthohumol per kg body weight rat
≙0.81 mg xanthohumol per kg body weight human.

Based on a body weight of 70 kg, the resulting daily dose for humans is:

Xanthohumol:
((5:37)·6)·70=56.76 mg xanthohumol per person per day

On this basis, the amount of solubilizate for the daily dose for a person is resulting as follows. The following calculation was carried out for a 10% xanthohumol solubilizate.

Xanthohumol: 56.76 mg·10=567.60 mg solubilizate

For polysorbate, this results in:

567.60 mg solubilizate·0.75=425.70 mg polysorbate in the total amount of solubilizate.

Assuming a body weight of 70 kg and given the WHO recommendation of a daily intake of 25 mg polysorbate (=1,750 mg polysorbate/day), the solubilizates described above are all within the acceptable daily intake (ADI) recommended by the WHO.

Prof. Dr. M. T. Khayyal from the University of Cairo, Faculty of Pharmacy at the Institute for Pharmacology, performed studies on the anti-inflammatory effect of curcumin and of combinations of curcumin with xanthohumol, in the native form and in the solubilized form according to the invention in each case.

Anti-inflammatory markers and antioxidant capacity were determined. Female Wistar rats with a body weight between 150 and 200 g were exposed to adjuvant induced arthritis according to Pearson et al. (1956). At day 0, the animals were administered 0.1 ml of Freund's Adjuvant (FCA) in the right hind paw, by subplantar injection. The animals were randomly divided into 12 groups of 8 animals each.

Group 1 was the control group.

Group 2 received diclofenac as a reference drug in a dose of 3 mg/kg body weight.

Group 7 received native xanthohumol in a dose of 5 mg/kg body weight, and

Group 8 received solubilized xanthohumol in the same dose.

Group 12 received a mixture of solubilized curcumin and solubilized xanthohumol, each in the same dose.

All extracts or solubilizates were administered orally once daily from day 0 through day 21 following the vaccination with the adjuvant. After day 21, the animals were killed and serum samples were prepared and stored at −80° C. Measurements were made of myeloperoxidase (MPO), C-reactive protein (CRP), total antioxidant capacity (TAC), and thiobarbituratic acid reactive substances (TBARS).

The results of the studies will now be explained with reference to the accompanying FIGS. 5 and 6.

First, the effects on C-reactive protein (CRP) were studied. C-reactive protein is a specific marker for anti-inflammatory activity. Xanthohumol alone has an effect comparable to that of diclofenac and showed better anti-inflammatory activity in its solubilized form compared to the native form (FIG. 5).

Myeloperoxidase (MPO) in plasma plays a central role as a pro-inflammatory mediator in rheumatoid arthritis and is an indicator for the invasion of neutrophil granulocytes into the affected tissue. Its concentration is elevated in patients with rheumatoid arthritis and causes oxidative stress. The native form of xanthohumol per se had only a slight effect on the serum concentration of MPO, while the solubilized form of xanthohumol is almost as efficient as diclofenac (FIG. 6).

Oxidative stress is one of the major factors contributing to joint destruction in rheumatoid arthritis (RA). An increase in the production of reactive oxygen species (ROS) leads to a reduced supply of endogenous antioxidants and ultimately results in the destruction of cells. The neutrophil granulocytes released in the rheumatoid joint produce free oxygen radicals which cause increased formation of lipid peroxides manifesting in an increase in serum TBARS. Therefore, an increase in antioxidant status represented by an increase in TAC can be used as an indication of protection against the development of degenerative inflammatory processes. The TAC and TBARS levels are inversely related to one another, i.e. a high level of antioxidant capacity TAC corresponds to a low TBARS concentration.

The following table contains data on the effect of curcumin and xanthohumol in native and in solubilized form, administered either alone or in combination with diclofenac in a dose of 3 mg per kg body weight once daily for 21 days, on the antioxidant capacity TAC and the thiobarbituric acid reactive substances TBARS in the serum of arthritic rats (n=8). Indicated are mean values±standard error of the mean (SEM).

| Group | TAC (nmol/microliter) | TBARS (nmol/l) |
| --- | --- | --- |
| Arthritic control group | 57.26 ± 3.36 | 13.10 ± 0.39 |
| Diclofenac (3 mg/kg) | 82.08 ± 2.96 | 7.93 ± 0.84 |
| Native xanthohumol (5 mg/kg) | 63.71 ± 1.02 | 11.42 ± 1.16 |
| Solubilized xanthohumol (5 mg/kg) | 81.74 ± 1.71 | 7.47 ± 0.53 |
| Native curcumin (5 mg/kg) ± xanthohumol (5 mg/kg) | 66.71 ± 1.27 | 11.74 ± 0.48 |
| Solubilized curcumin (5 mg/kg) + xanthohumol (5 mg/kg) | 82.22 ± 1.53 | 7.90 ± 0.59 |

Xanthohumol solubilized according to the invention alone was almost as effective as diclofenac in reducing TBARS and increasing TAC in the serum of arthritic rats, as the data in the table show.

Due to the small particle sizes as measured, advantageously, a liquid is formed which is clear in particular in terms of perception with the human eye.

The clarity of the solubilizate can also be demonstrated by its low turbidity. For this purpose, the following working hypothesis is applied: The clearer an aqueous dilution of a solubilizate or of another formulation of xanthohumol or of xanthohumol with curcumin, in particular under physiological conditions of a gastric passage, i.e. at a pH of 1.1 and a temperature of 37° C., the better is its solubilization. The better the solubilization, the better is the bioavailability of the active substances or of the product containing them.

This bioavailability can already be deduced from the particularly low turbidity of the solubilizate, which can be considered as a kind of parameter for bioavailability.

Without additives as in soft and hard gelatin capsules, the transparent and completely stably water-soluble formulation according to the invention exhibits stable transparency in gelatin-free capsules (hard and/or soft) and in water-based liquid end products, regardless of the pH.

Products exhibiting such transparency and water solubility are urgently sought by the relevant industry for innovative products as a capsule filling. To the knowledge of the inventor, a formulation of xanthohumol or xanthohumol with curcumin, which meets these requirements has not yet been known.

As a result of the formulation according to the invention in a solubilizate with very small, stable and gastric acid-resistant micelles, the invention provides a solubilizate of xanthohumol or xanthohumol with curcumin for use as a dietary supplement and/or as a pharmaceutical drug, in particular for use as a dietary supplement and/or as a pharmaceutical drug that has an anti-inflammatory effect.

It will be apparent to a person skilled in the art that the invention is not limited to the examples described above, but rather can be varied in multiple ways. It is in particular possible for the features of the individually illustrated examples to be combined or swapped.

The invention claimed is:

1. An anhydrous solubilizate, consisting of:
    xanthohumol with a content of less than or equal to 35 wt. %, the xanthohumol being derived from an extract of hops;
    at least 45 wt. % of an emulsifier with an HLB value in the range between 13 and 18;
    between 0 and 35 wt. % of ethanol; and
    between 0 and 25 wt. % of glycerol.

2. The solubilizate as in claim 1,
    wherein the extract of hops is an ethanolic extract of hard resins from hops, a concentration of xanthohumol in the extract being in a range between 60 wt. % and 95 wt. %.

3. The solubilizate as in claim 1,
    wherein the emulsifier is polysorbate 80 or polysorbate 20 or a mixture of polysorbate 20 and polysorbate 80; or
    wherein the emulsifier is a sucrose ester of an edible fatty acid or a mixture of at least two sucrose esters of edible fatty acids; or
    wherein the emulsifier is a mixture of polysorbate 80 or polysorbate 20 or a mixture of polysorbate 80 and polysorbate 20 with at least one sucrose ester of an edible fatty acid; or
    wherein the emulsifier is a mixture of at least one phospholipid, in particular lecithin, with at least one sucrose ester of an edible fatty acid.

4. The solubilizate as in claim 1, wherein
    a ratio of emulsifier to xanthohumol is in a range between 30:1 and 3:1.

5. The solubilizate as in claim 1, wherein
    a content of the emulsifier is at least 45 wt. %.

6. The solubilizate as in claim 1, wherein
    a diameter distribution of micelles in a dilution of the solubilizate with distilled water in a ratio of 1:500 at pH 1.1 and 37° C. ranges from d10=70 nm to d90=160 nm.

7. The solubilizate as in claim 1, wherein
    the solubilizate has a turbidity of less than 100 FNU as measured by scattered light measurement using infrared light in compliance with the specifications of the ISO 7027 standard at a dilution of the solubilizate in a ratio of 1:50 in water at pH 1.1 and 37° C.

8. A capsule filled with the anhydrous solubilizate as in claim 1, wherein the capsule is in the form of a soft gelatin capsule or a hard gelatin capsule or a soft gelatin-free capsule or a hard gelatin-free capsule.

9. A fluid, comprising the anhydrous solubilizate as in claim 1, wherein the fluid is selected from the group consisting of foods, cosmetics, and pharmaceutical products.

10. A method for treating diseases involving inflammation, cancer, Alzheimer's, Parkinson's, obesity, high cholesterol levels, elevated blood sugar, diabetes, metabolic syndrome and/or autoimmune diseases, multiple sclerosis (MS), for reducing visceral fat, for thermogenesis, for lowering cholesterol and/or for lowering glucose in the blood and/or triglycerides in the blood, for improving macular pigment density, for reducing oxidative stress and/or for reducing an accumulation of fat in the hepatocytes, for treating Friedreich's ataxia, lysosomal diseases, arteriosclerosis, heart diseases, arthritis, comprising:

administering to a patient the solubilizate as in claim 1.

11. The method of claim 10, wherein the solubilizate is administered to the patient with a dose of xanthohumol in a range from 0.5 mg/kg body weight to 1 mg/kg body weight.

12. A method for producing a solubilizate as in claim 1, comprising:
   (a) providing at least one emulsifier with an HLB value in a range between 13 and 18;
   (b) adding ethanol;
   (c) heating to a temperature of up to 85° C. while mixing;
   (d) adding an ethanolic extract of hard resins from hops while mixing;
   wherein step (d) comprises heating to a temperature in a range from 81° C. to 90° C.

13. The method as in claim 12, wherein step (b) is preceded by a step
   (b1) of dissolving in ethanol the ethanolic extract of the hard resins from hops while heating to a temperature in a range from 40° C. to 62° C.

14. The method of claim 13, wherein
   step (c) comprises heating to a lower temperature in a range from 40° C. to 62° C.

15. The method of claim 13, wherein
   step (b) comprises adding a phospholipid together with ethanol.

16. The method as in claim 13, wherein
   step (b) comprises adding glycerol together with ethanol.

* * * * *